US010625009B2

(12) United States Patent
Perry et al.

(10) Patent No.: US 10,625,009 B2
(45) Date of Patent: Apr. 21, 2020

(54) AIRTRAP, SYSTEM AND METHOD FOR REMOVING MICROBUBBLES FROM A FLUID STREAM

(71) Applicants: Baxter International Inc., Deerfield, IL (US); Baxter Healthcare SA, Glattpark (Opfikon) (CH)

(72) Inventors: Mark Perry, McHenry, IL (US); Jorge DelCastillo, Des Plaines, IL (US); Matthew Muller, Lindenhurst, IL (US); Carlos Corrales, Vernon Hills, IL (US); Atif Yardimci, Lake Forest, IL (US); James Laird, Grayslake, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 127 days.

(21) Appl. No.: 15/046,048

(22) Filed: Feb. 17, 2016

(65) Prior Publication Data
US 2017/0232173 A1    Aug. 17, 2017

(51) Int. Cl.
*A61M 1/14*    (2006.01)
*A61M 5/36*    (2006.01)
(Continued)

(52) U.S. Cl.
CPC ............ *A61M 1/1658* (2013.01); *A61M 1/28* (2013.01); *A61M 1/3486* (2014.02);
(Continued)

(58) Field of Classification Search
CPC .... A61M 1/1658; A61M 1/3638; A61M 1/28; A61M 1/3627; A61M 5/142; A61M 5/36;
(Continued)

(56) References Cited

U.S. PATENT DOCUMENTS 250,868 A    12/1881    Abbott
927,476 A    7/1909    Barker
(Continued)

FOREIGN PATENT DOCUMENTS

CN    1 569 265    1/2005
DE    2 544 258    4/1977
(Continued)

OTHER PUBLICATIONS

International Search Report—PCT/US2017/015332 dated Jul. 4, 2017—5 pages.
(Continued)

*Primary Examiner* — Kevin C Sirmons
*Assistant Examiner* — Tezita Z Watts
(74) *Attorney, Agent, or Firm* — K&L Gates LLP

(57) ABSTRACT

An airtrap for a medical or physiological fluid in one embodiment includes a conical housing having a radius that increases from its top to its bottom when the housing is positioned for operation; a medical or physiological fluid inlet located at an upper portion of the conical housing; a medical or physiological fluid outlet located at a lower portion of the conical housing, the inlet and the outlet positioned and arranged so that medical or physiological fluid spirals in an increasing arc around an inside of the conical housing downwardly from the inlet to the outlet; and a gas collection area located at an upper portion of the conical housing. In another embodiment, the airtrap is shaped like a seahorse having a head section and a tail section. Any of the airtraps herein may be used for example in blood sets, peritoneal dialysis cassette tubing, and drug delivery sets.

24 Claims, 7 Drawing Sheets

(51) Int. Cl.
  *A61M 1/16* (2006.01)
  *A61M 5/38* (2006.01)
  *A61M 1/28* (2006.01)
  *A61M 1/36* (2006.01)
  *B01D 19/00* (2006.01)
  *A61M 1/34* (2006.01)

(52) U.S. Cl.
  CPC ........ *A61M 1/3627* (2013.01); *A61M 1/3638* (2014.02); *A61M 1/3679* (2013.01); *A61M 5/36* (2013.01); *A61M 5/385* (2013.01); *B01D 19/0057* (2013.01); *A61M 2205/123* (2013.01); *A61M 2205/7536* (2013.01); *A61M 2206/16* (2013.01)

(58) Field of Classification Search
  CPC ............ A61M 5/385; A61M 2205/123; A61M 2205/7536; A61M 2206/16; B01D 19/0057
  See application file for complete search history.

(56) References Cited

U.S. PATENT DOCUMENTS

| | | |
|---|---|---|
| 1,505,050 A | 8/1924 | Lauritsen |
| 1,867,465 A | 7/1932 | Moynan |
| 2,292,007 A | 8/1942 | Morgan |
| 3,044,236 A | 7/1962 | Bearden et al. |
| 3,074,645 A | 1/1963 | Main |
| 3,088,595 A | 5/1963 | Robb |
| 3,095,062 A | 6/1963 | Neely |
| 3,229,445 A | 1/1966 | Kraft |
| 3,287,885 A | 11/1966 | Sommer |
| 3,295,297 A | 1/1967 | Collins |
| 3,342,019 A | 9/1967 | Smythe |
| 3,352,779 A | 11/1967 | Austin et al. |
| 3,412,760 A | 11/1968 | Franck |
| 3,527,572 A | 9/1970 | Urkiewicz |
| 3,579,441 A | 5/1971 | Brown |
| 3,581,464 A | 6/1971 | Bhuta et al. |
| 3,598,727 A | 8/1971 | Wilock |
| 3,677,710 A | 7/1972 | Hirsch |
| 3,709,222 A | 1/1973 | DeVries |
| 3,744,492 A | 7/1973 | Leibinsohn |
| 3,751,879 A | 8/1973 | Allington |
| 3,769,207 A | 10/1973 | Baer |
| 3,771,288 A | 11/1973 | Wisman et al. |
| 3,795,088 A | 3/1974 | Esmond |
| 3,827,561 A | 8/1974 | Serfass et al. |
| 3,834,386 A | 9/1974 | Sisley |
| 3,849,071 A | 11/1974 | Kayser |
| 3,878,095 A | 4/1975 | Fraiser et al. |
| 3,898,045 A | 8/1975 | Bowley |
| 3,908,653 A | 9/1975 | Kettering |
| 3,920,556 A | 11/1975 | Bowman |
| 3,946,731 A | 3/1976 | Lichtenstein |
| 3,964,479 A | 6/1976 | Boag et al. |
| 3,976,311 A | 8/1976 | Spendlove |
| 3,982,538 A | 9/1976 | Sharpe |
| 3,985,134 A | 10/1976 | Lissot et al. |
| 3,985,135 A | 10/1976 | Carpenter et al. |
| 3,996,027 A * | 12/1976 | Schnell ............... A61M 1/3627 95/261 |
| 4,009,715 A | 3/1977 | Forberg et al. |
| 4,026,669 A | 5/1977 | Leonard et al. |
| 4,031,891 A | 6/1977 | Jess |
| 4,031,894 A | 6/1977 | Jess |
| 4,038,190 A | 7/1977 | Baudet et al. |
| 4,047,563 A | 9/1977 | Kurata |
| 4,048,995 A | 9/1977 | Mittleman |
| 4,054,522 A | 10/1977 | Pinkerton |
| 4,061,031 A | 12/1977 | Grimsrud |
| 4,102,655 A | 7/1978 | Jeffrey et al. |
| 4,137,160 A | 1/1979 | Ebing et al. |
| 4,149,860 A | 4/1979 | Kulik |
| 4,151,088 A | 4/1979 | Wolf, Jr. et al. |
| 4,157,965 A * | 6/1979 | Raible ................. A61M 1/3627 210/305 |
| 4,190,426 A * | 2/1980 | Ruschke ................. A61M 5/36 96/6 |
| 4,191,182 A | 3/1980 | Popovich et al. |
| 4,200,095 A | 4/1980 | Reti |
| 4,231,370 A | 11/1980 | Mroz |
| 4,279,626 A | 7/1981 | Buchmiller et al. |
| 4,293,413 A | 10/1981 | Schnell |
| 4,304,670 A | 12/1981 | Watanabe et al. |
| 4,311,137 A | 1/1982 | Gerard |
| 4,325,715 A | 4/1982 | Bowman et al. |
| 4,344,777 A | 8/1982 | Siposs |
| 4,345,919 A | 8/1982 | Wilkinson et al. |
| 4,345,999 A | 8/1982 | Sigdell et al. |
| 4,353,368 A | 10/1982 | Slovak et al. |
| 4,363,641 A | 12/1982 | Finn, III |
| 4,368,118 A | 1/1983 | Siposs |
| 4,370,983 A | 2/1983 | Lichtenstein |
| 4,390,351 A | 6/1983 | Matsui et al. |
| 4,411,792 A | 10/1983 | Babb |
| 4,424,068 A | 1/1984 | McMillan |
| 4,427,009 A | 1/1984 | Wells et al. |
| 4,433,971 A | 2/1984 | Lindsay et al. |
| 4,436,620 A | 3/1984 | Bellotti et al. |
| 4,439,189 A | 3/1984 | Sargeant et al. |
| 4,468,329 A | 8/1984 | Shaldon et al. |
| 4,486,188 A | 12/1984 | Altshuler et al. |
| 4,493,705 A | 1/1985 | Gordon et al. |
| 4,512,163 A | 4/1985 | Wells et al. |
| 4,531,937 A | 7/1985 | Yates |
| 4,568,333 A | 2/1986 | Sawyer et al. |
| 4,583,981 A | 4/1986 | Urquhart et al. |
| 4,586,925 A | 5/1986 | Carlsson et al. |
| 4,622,032 A | 11/1986 | Katsura et al. |
| 4,643,713 A | 2/1987 | Viitala |
| 4,643,715 A | 2/1987 | Isono et al. |
| 4,666,598 A | 5/1987 | Heath et al. |
| 4,681,606 A | 7/1987 | Swan, Jr. et al. |
| 4,690,762 A | 9/1987 | Katsura |
| 4,702,829 A | 10/1987 | Polaschegg et al. |
| 4,711,715 A | 12/1987 | Polaschegg et al. |
| 4,715,959 A | 12/1987 | Allan et al. |
| 4,722,725 A | 2/1988 | Sawyer et al. |
| 4,722,731 A | 2/1988 | Vailancourt |
| 4,734,269 A | 3/1988 | Clarke et al. |
| 4,770,769 A | 9/1988 | Schael |
| 4,770,787 A | 9/1988 | Heath et al. |
| 4,798,090 A | 1/1989 | Heath et al. |
| 4,806,135 A * | 2/1989 | Siposs ................. A61M 1/3627 210/304 |
| 4,838,865 A | 6/1989 | Flank et al. |
| 4,860,591 A | 8/1989 | Garland |
| 4,932,987 A | 6/1990 | Molina |
| 4,941,875 A | 7/1990 | Brennan |
| 4,946,439 A | 8/1990 | Eggers |
| D311,061 S | 10/1990 | Vrana et al. |
| 4,964,984 A | 10/1990 | Reeder et al. |
| 4,976,685 A | 12/1990 | Block, Jr. |
| 4,997,464 A | 3/1991 | Kopf |
| 4,997,570 A | 3/1991 | Polaschegg |
| 5,024,756 A | 6/1991 | Sternby |
| 5,047,147 A | 9/1991 | Chevallet et al. |
| 5,049,492 A | 9/1991 | Sauer et al. |
| 5,059,173 A | 10/1991 | Sacco |
| 5,061,236 A | 10/1991 | Sutherland et al. |
| 5,061,365 A | 10/1991 | Utterberg |
| 5,098,407 A | 3/1992 | Okamura |
| 5,112,480 A | 5/1992 | Hukasawa |
| 5,167,921 A | 12/1992 | Gordon |
| 5,178,656 A | 1/1993 | Schott |
| 5,178,763 A | 1/1993 | Delaunay |
| 5,203,891 A | 4/1993 | Lema |
| 5,204,000 A | 4/1993 | Steadman et al. |
| 5,211,849 A | 5/1993 | Kitaevich et al. |
| 5,228,889 A | 7/1993 | Cortial et al. |
| 5,246,560 A | 9/1993 | Nekoksa et al. |

(56) References Cited

U.S. PATENT DOCUMENTS

| | | |
|---|---|---|
| 5,247,434 A | 9/1993 | Peterson et al. |
| 5,268,077 A | 12/1993 | Bubik et al. |
| 5,326,476 A | 7/1994 | Grogan et al. |
| 5,328,461 A | 7/1994 | Utterberg |
| 5,356,376 A | 10/1994 | Milijasevic et al. |
| 5,358,481 A | 10/1994 | Todd et al. |
| 5,364,371 A | 11/1994 | Kamen |
| 5,368,555 A | 11/1994 | Sussman et al. |
| 5,394,732 A | 3/1995 | Johnson et al. |
| 5,411,705 A | 5/1995 | Thor et al. |
| 5,421,815 A | 6/1995 | Noguchi et al. |
| 5,429,595 A | 7/1995 | Wright, Jr. et al. |
| 5,441,636 A | 8/1995 | Chevallet et al. |
| 5,468,388 A | 11/1995 | Goddard et al. |
| 5,489,385 A | 2/1996 | Raabe et al. |
| 5,503,801 A | 4/1996 | Brugger |
| 5,509,895 A | 4/1996 | Noguchi et al. |
| 5,520,640 A | 5/1996 | Utterberg |
| 5,534,118 A * | 7/1996 | McCutchen ............. B01D 3/10 202/205 |
| 5,578,070 A | 11/1996 | Utterberg |
| 5,591,251 A | 1/1997 | Brugger |
| 5,605,540 A | 2/1997 | Utterberg |
| 5,622,545 A | 4/1997 | Mazzei et al. |
| 5,632,894 A * | 5/1997 | White .................... B01D 29/21 210/436 |
| 5,637,081 A | 6/1997 | Noguchi et al. |
| 5,643,205 A | 7/1997 | Utterberg |
| 5,650,071 A | 7/1997 | Brugger et al. |
| 5,674,199 A | 10/1997 | Brugger |
| 5,681,294 A | 10/1997 | Osborne et al. |
| 5,683,355 A | 11/1997 | Fini et al. |
| 5,730,730 A | 3/1998 | Darling, Jr. |
| 5,763,266 A | 6/1998 | Palsson et al. |
| 5,776,091 A | 7/1998 | Brugger et al. |
| 5,800,597 A | 9/1998 | Perrotta et al. |
| 5,830,185 A | 11/1998 | Block, Jr. |
| 5,849,065 A | 12/1998 | Wojke |
| 5,851,202 A | 12/1998 | Carlsson |
| 5,858,239 A | 1/1999 | Kenley et al. |
| 5,863,421 A | 1/1999 | Peter, Jr. et al. |
| 5,895,368 A | 4/1999 | Utterberg |
| 5,928,889 A | 7/1999 | Bakich et al. |
| 5,931,990 A | 8/1999 | Andrews |
| 5,951,870 A | 9/1999 | Utterberg |
| 5,980,741 A | 11/1999 | Schnell et al. |
| 5,983,947 A | 11/1999 | Utterberg |
| 5,989,318 A | 11/1999 | Schroll |
| 6,010,623 A | 1/2000 | Schnell et al. |
| 6,019,824 A | 2/2000 | Schnell |
| 6,046,806 A | 4/2000 | Thompson |
| 6,051,134 A | 4/2000 | Schnell et al. |
| 6,053,967 A | 4/2000 | Heilmann et al. |
| 6,066,111 A | 5/2000 | Brockhoff |
| 6,071,269 A | 6/2000 | Schnell et al. |
| 6,117,342 A | 9/2000 | Schnell et al. |
| 6,171,484 B1 | 1/2001 | Schnell et al. |
| 6,176,903 B1 | 1/2001 | Wamsiedler |
| 6,187,198 B1 | 2/2001 | Utterberg |
| 6,206,954 B1 | 3/2001 | Schnell et al. |
| 6,238,808 B1 | 5/2001 | Arao et al. |
| 6,251,167 B1 | 6/2001 | Berson |
| 6,312,414 B1 | 11/2001 | Brockhoff et al. |
| 6,344,139 B1 | 2/2002 | Utterberg |
| 6,357,600 B1 | 3/2002 | Scagliarini |
| 6,391,541 B1 | 5/2002 | Petersen et al. |
| 6,391,638 B1 | 5/2002 | Shaaltiel |
| 6,464,878 B2 | 10/2002 | Utterberg |
| 6,481,455 B2 | 11/2002 | Gustafson et al. |
| 6,514,255 B1 | 2/2003 | Ferree |
| 6,517,732 B1 | 2/2003 | Brockoff et al. |
| 6,537,356 B1 | 3/2003 | Soriano |
| 6,562,107 B2 | 5/2003 | Purdom et al. |
| 6,755,801 B2 | 6/2004 | Utterberg et al. |
| 6,827,862 B1 | 12/2004 | Brockhoff et al. |
| 7,842,123 B2 | 11/2010 | Milo et al. |
| 8,187,466 B2 | 5/2012 | Folden et al. |
| 8,303,856 B2 | 11/2012 | Jang et al. |
| 8,444,586 B2 | 5/2013 | Beck |
| 8,747,342 B2 | 6/2014 | Caleffi et al. |
| 9,028,691 B2 | 5/2015 | Grant et al. |
| 2001/0042441 A1 | 11/2001 | Purdom et al. |
| 2002/0091350 A1 | 7/2002 | Belson |
| 2002/0114731 A1 | 8/2002 | Stringer |
| 2004/0019312 A1 | 1/2004 | Childers et al. |
| 2004/0019313 A1 | 1/2004 | Childers et al. |
| 2005/0131332 A1 | 6/2005 | Kelly et al. |
| 2005/0247203 A1 | 11/2005 | Chevallet et al. |
| 2006/0137663 A1 | 6/2006 | Vaught |
| 2009/0012449 A1 * | 1/2009 | Lee .................. A61M 1/28 604/29 |
| 2009/0137941 A1 | 5/2009 | Lynch et al. |
| 2009/0199708 A1 | 8/2009 | Milo et al. |
| 2014/0276376 A1 * | 9/2014 | Rohde ................ A61M 1/1656 604/29 |
| 2014/0373711 A1 | 12/2014 | Cassidy et al. |

FOREIGN PATENT DOCUMENTS

| | | |
|---|---|---|
| DE | 32 02 582 | 9/1982 |
| DE | 32 15 003 | 11/1983 |
| DE | 102005001779 | 9/2006 |
| EP | 0 058 325 | 8/1982 |
| EP | 0 062 913 | 10/1982 |
| EP | 0 143 340 | 6/1985 |
| EP | 0 318 993 | 6/1989 |
| EP | 0 350 675 | 1/1990 |
| EP | 0 106 026 | 6/1990 |
| EP | 0 587 251 | 3/1994 |
| EP | 0 614 675 | 9/1994 |
| EP | 0614675 A1 | 9/1994 |
| EP | 0 800 838 | 10/1997 |
| EP | 0 808 633 | 11/1997 |
| EP | 0 776 222 | 4/2003 |
| EP | 1 600 184 | 11/2005 |
| EP | 1 944 386 | 7/2008 |
| FR | 2 344 297 | 10/1977 |
| FR | 2 345 165 | 10/1977 |
| GB | 1 408 319 | 10/1975 |
| GB | 1 554 810 | 10/1979 |
| GB | 2 041 233 | 9/1980 |
| GB | 2 061 755 | 5/1981 |
| GB | 2 063 108 | 6/1981 |
| GB | 2 212 739 | 8/1989 |
| NL | 7 701 451 | 5/1977 |
| WO | 97/40870 | 11/1997 |
| WO | 98/23353 | 6/1998 |
| WO | 2005/044340 | 5/2005 |
| WO | 2005/089832 | 9/2005 |
| WO | 2006/120415 | 11/2006 |

OTHER PUBLICATIONS

Written Opinion of the International Searching Authority—PCT/US2017/015332 dated Jul. 4, 2017—10 pages.

* cited by examiner

AIRTRAP, SYSTEM AND METHOD FOR REMOVING MICROBUBBLES FROM A FLUID STREAM

CROSS-REFERENCE TO RELATED APPLICATIONS

This application is related in subject matter to commonly owned (i) U.S. Pat. No. 7,871,462, issued Jan. 18, 2011, entitled "Dialysis Systems Having Air Separation Chambers with Internal Structures to Enhance Air Removal", filed Oct. 1, 2007; (ii) U.S. Pat. No. 7,892,331, issued Feb. 22, 2011, entitled "Dialysis Systems Having Air Separation Chambers with Internal Structures to Enhance Air Removal", filed Oct. 1, 2007; (iii) U.S. Pat. No. 7,892,332, issued Feb. 22, 2011, entitled "Dialysis Systems Having Airtraps with Internal Structures to Enhance Air Removal", filed Oct. 1, 2007; (iv) U.S. Pat. No. 7,988,768, issued Aug. 2, 2011, entitled "Dialysis Systems Having Spiraling Fluid Air Separation Chambers", filed Dec. 28, 2010; (v) U.S. Pat. No. 8,025,716, issued Sep. 27, 2011, entitled "Fluid Delivery Systems and Methods Having Floating Baffle Aided Air Removal", filed Feb. 18, 2011; (vi) U.S. Pat. No. 8,080,091, issued Dec. 20, 2011, entitled "Dialysis Systems and Methods Including Cassette with Fluid Heating and Air Removal", filed Feb. 18, 2011, and (vii) U.S. Pat. No. 8,221,529, issued Jul. 17, 2012, entitled "Dialysis Systems and Methods Including Cassette With Air Removal", filed Feb. Nov. 21, 2011.

BACKGROUND

The present disclosure relates generally to air removal devices, systems and methods for liquid delivery systems. More specifically, the present disclosure relates to air removal devices, systems and methods for medical fluid delivery, such as blood, dialysis fluid, substitution fluid or intravenous drug delivery.

Due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products than a patient receiving less frequent but perhaps longer treatments. A patient receiving more frequent treatments does not experience as much of a down cycle as does an in-center patient, who has built-up two or three days worth of toxins prior to a treatment. In certain areas, the closest dialysis center can be many miles from the patient's home causing door-to-door treatment time to consume a large portion of the day. HHD can take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In any of the above modalities, entrained air and other gases are a concern. Entrained air can cause inaccuracies when pumping dialysis fluid for any of PD, HD, HF, HDF, other blood treatment modalities such continuous renal replacement therapy ("CRRT") treatment, and intravenous drug delivery. Entrained air can cause a reduction in effective surface area in a hemodialysis filter when it accumulates on the filter fibers, leading to a reduction in effectiveness of the therapy. Entrained air entering a patient's peritoneum during PD can cause discomfort.

Regarding an extracorporeal blood therapy (e.g. HD, HF, HDF, CRRT), a gas phase may be present in the blood arising from leakage into an otherwise closed system from the outside (e.g. air sucked in via pumping), residual air not effectively primed from the device at the start of therapy, gas evolving from the blood plasma and cellular compartments (e.g. oxygen, carbon dioxide and nitrogen), and/or gas transported across a membrane from the dialysis fluid side (e.g. carbon dioxide from bicarbonate solution). While different gases may dominate in certain situations, air (78% nitrogen, 21% oxygen, 1% others) is the most typical gas. The term "air" as used herein may mean air (78% nitrogen, 21% oxygen, 1% others), while the term gas includes air and/or any other gas, e.g., carbon dioxide.

An air embolism during a blood treatment may occur when a bolus of air is infused into the patient. As little as 20 ml of air can be dangerous when introduced directly into the patient's blood system. One of the most common risks for a venous air embolism is an empty intravenous ("IV") saline bag during rapid infusions for cramps and during a final blood rinse-back.

Microbubbles circulating in the extracorporeal circuit may present hazards when returned to patients. Microbubbles may originate in extracorporeal tubing, circulate in the blood stream until lodging in the capillary bed of various organs, mainly the lungs. During its course within the capillary, a bubble abrades the glycocalyx layer lining the surface of the vessels and thereafter obstructs blood flow through the capillary. This causes tissue ischemia, inflammatory response, and complement activation. Aggregation of platelets and clot formation may occur as well, leading to further obstruction of the microcirculation and subsequent tissue damage.

Microbubbles in the extracorporeal circuit may also contribute to platelet activation, fouling of blood-wetted surfaces with protein deposits, and flow blockages. Accumulation of bubbles in blood set recirculation zones may form foam having a high surface area, which accelerates clotting. Clots block flow through dialyzer fibers and the return fistula needle. Gas bubble induced clotting may also limit the reuse of dialyzers and blood sets.

Dialysis patients using catheter-based treatments are at the highest risk of venous air embolism since any air is introduced directly into the central blood vessels immediately. Ensuring that the catheter is clamped securely before connecting or disconnecting bloodlines limits the risk of venous air embolism. However, a venous catheter crack or disconnection may go unnoticed.

It should also be appreciated that air may be an issue for other treatments requiring the delivery of a fluid to a patient, such as PD and intravenous drug delivery.

For each of the above reasons and scenarios, a need exists to provide an apparatus that ensures that entrained air is removed from blood, dialysis fluid, substitution fluid or an intravenous drug during treatment and prior to delivering or returning such fluids to the patient.

SUMMARY

The examples described herein disclose air removal devices, systems and methods applicable, for example, to fluid delivery for: plasmapherisis, hemodialysis ("HD"), hemofiltration ("HF") hemodiafiltration ("HDF"), and continuous renal replacement therapy ("CRRT") treatments. The air removal devices, systems and methods described herein are also applicable to peritoneal dialysis ("PD") and to intravenous drug delivery. These modalities may be referred to collectively or generally individually as medical fluid delivery.

Moreover, each of the devices, systems and methods described herein may be used with clinical or home-based machines. For example, the systems may be employed in in-center HD, HF or HDF machines, which run throughout the day. Alternatively, the systems may be used with home HD, HF or HDF machines, which are operated at the patient's convenience. One such home system is described in U.S. Pat. No. 8,029,454 ("the '454 patent"), issued Oct. 4, 2011, entitled "High Convection Home Hemodialysis/Hemofiltration And Sorbent System", filed Nov. 4, 2004, assigned to the assignee of the present application. Another such home system is described in U.S. Pat. No. 8,721,884 ("the '884 patent"), issued May 13, 2014, entitled "Hemodialysis Systems and Methods", filed Feb. 7, 2013. The entire contents of each of the above references is incorporated herein by reference and relied upon.

The air removal devices, systems and methods described herein prevent large bolus injections of gas from being infused into the patient, which may result in a pulmonary embolism. The risks of microemboli that may result from infusion of microbubbles are not as clear. The smaller bubbles may be digested in the venous system or be passed through the pulmonary bed. In any case, the air removal devices, systems and methods described herein also seek to remove microbubbles from blood or medical fluid before being infused into the patient.

The airtraps discussed herein seek to minimize extracorporeal blood clotting. The airtraps may accordingly use blood compatible materials, minimize gas foaming, resist clot attachment to surfaces, avoid blood recirculation and stagnation, and seek to minimize blood/material contact surface area. For certain applications, the airtraps are disinfected between uses and reused, e.g., thirty times or more. The airtrap materials are therefore selected to survive and function after disinfection, e.g., a chemical disinfection and/or a heat disinfection treatment of approximately 80° C. to 90° C. over multiple, e.g., thirty, disinfections or cycles. The airtraps are constructed in an embodiment to resist clots attaching to their surfaces, maximize wall shear when a wash mode is used to effectively remove clots, and maintain a robust integral mechanical and microbiological closure to withstand operating pressures. The airtraps may also be constructed to minimize extracorporeal blood or medical fluid volume, enhance the ability to be auto-primed, present minimal blood flow pressure drop, and be optimized for manufacturability.

The airtraps discussed herein in an embodiment have a large enough volume to accept trapped air developed over an entire medical fluid treatment. In alternative embodiments, the airtraps have a considerably smaller volume and instead employ an air removal technique. The air removal technique may be active, e.g., employ a sensor and one or more pump in communication with a controller. In another embodiment, the air removal technique is passive, e.g. employs a filter and/or valve that enables separated air to be purged via pressure built inside the airtrap. In a further alternative embodiment, the air removal technique is manual, e.g., includes a septum allowing air to be withdrawn via a needle.

In one embodiment, the airtrap includes a conically shaped housing. Blood or medical fluid enters through an inlet at the top of the conically shaped housing, flows around and spirals downward along an interior, ever-increasing diameter, conical wall of the housing and exits through an outlet at the bottom of the conically shaped housing. Entrained air is separated centrifically towards the center and is moved buoyantly upward. Air or gas accumulates in a quiet upper region of the conical housing, where it is held at pressure. In a passive air removal embodiment, the air may be held at pressure against a hydrophobic membrane and/or a check or one-way valve, e.g., silicone, which allow the air to be passively released from the housing, while preventing outside, non-sterile air from entering the airtrap. Typical pressures may be 100 to 300 mmHg at a blood or medical fluid flow rate of 400 ml/min. Gas passes through the membrane, while blood is retained.

The conical housing airtrap in an embodiment includes an interior housing cone that extends up into the exterior housing cone to provide further aid in the spiraling of the blood or medical fluid, aiding the centripetal removal of small gas bubbles. The conical housing airtrap improves the separation of gas from blood or medical fluid, which is ejected to atmosphere, while avoiding therapy interruption to manually aspirate air. The conical housing airtrap greatly reduces emboli risk and risk for micorembolis, thereby reducing risks for clots, tissue ischemia and inflammation. Since the airtrap effectively eliminates gas bubbles and microbubbles, the tendency for clotting in the extracorporeal set is diminished. The conical housing airtrap remains sterile or near sterile throughout treatment, does not affect system priming, prevents air ingress and employs blood compatible plastic and/or metal materials, such as silicone or medical grade stainless steel housing materials, polyvinylidene fluoride or polyvinylidene difluoride ("PVDF") or polysulfone membrane or filter materials, and silicone valve. Other materials, such as Kynar or silicone-based or silicone-coated materials may be employed alternatively for the housing.

In an alternative embodiment, the airtrap again has a conical shape, but here the cone narrows in diameter as it extends from top to bottom. The top of the cone extends down into itself, forming an inner obstruction or slender cone that extends within the outer housing cone. The outer and inner cone shapes cause fluid within the airtrap to spin in a vortex, creating a centripetal force that forces heavier fluid outwardly and lighter air to release at the inside of the airtrap and rise buoyantly to a quiet zone at the top of the conical housing. Degassed fluid exits the conical housing at its bottom. Blood or medical fluid flows in a circular path, spiraling down to the outlet, creating no eddy currents in an embodiment. A volume may be provided at the top of the housing to collect trapped air, which may also include a septum that is pierced by a syringe to pull air manually from the airtrap. The alternative conical airtrap may have a hydrophobic membrane and/or valve, and may be made of any of the materials discussed above.

In a further alternative embodiment, the airtrap has a housing shape similar to that of a seahorse. Blood or medical fluid potentially containing air enters at the top or enlarged head chamber of the seahorse housing. The blood or medical fluid spreads and slows, allowing gas bubbles to follow a gentle slow flow and to rise towards an upper ceiling of the head chamber. The gradually changing shape of the head chamber allows fluid flow to slow without forming eddies. Once blood or medical fluid flows past the head chamber, the fluid is directed downwardly through a bending and varying diameter of a tail section of the seahorse shape, allowing additional opportunity for gas bubbles to rise towards the head chamber ceiling. The chamber head and tail have no obstructions to cause eddies in an embodiment, so fluid flows through the seahorse airtrap, sweeping surfaces to minimize clotting. A hump may be provided on the top of the head chamber for storage volume for trapped air or gas. The streamline shape of the chamber head and seahorse tail minimizes blood volume and surface area contact. An alternative seahorse embodiments may have a hydrophobic membrane and/or valve, and may be made of the materials discussed above. Further alternatively, the seahorse embodiment includes a septum that may be pierced by a syringe to pull air manually from the airtrap.

Each of the airtrap embodiments described herein may be provided as part of a blood set with other components, such as an arterial line extending to a pumping chamber (membrane or peristaltic), which extends to an arterial end of a dialyzer. A venous line extends from a venous end of the dialyzer. One of the airtraps is provided in the venous line in an embodiment. A second (same or different airtrap) may optionally be placed in the arterial line, e.g., between the blood pump and dialyzer so that the airtrap is under positive pressure. The blood set may be single use or configured for being disinfected between treatments and reused over multiple treatments. In an embodiment, the airtrap housing has clipping or grabbing structure formed with or attached to the outer wall of the housing of the airtrap, so that the airtrap may be clipped removeably to or grabbed removeably by a blood treatment machine.

In a peritoneal dialysis application, any of the airtraps described herein may be employed as part of the patient line extending from the peritoneal dialysis machine to the patient. The airtrap may be placed at a machine end of the patient line, so that the airtrap may be clipped removeably to or grabbed removeably by the peritoneal dialysis machine. The airtrap traps air going and coming from the patient. Fluid coming from the patient will be under negative pressure, such that a one-way valve will likely be sealed shut. Trapped air may be purged however during the next fill cycle when the patient line is under positive pressure.

In an intravenous drug delivery embodiment, the airtrap may be placed in the patient line upstream or downstream of the drug delivery pump (e.g., rotary peristaltic, linear peristaltic, or shuttle), so that fluid within the airtrap is under positive pressure. Placement of the airtrap upstream of the drug delivery pump traps air prior to entering the pump, which can cause therapy-interrupting alarms when sensed. The pulsatile filling portion of the peristaltic pump stroke may reduce pressure causing the one-way valve to seal shut and temporarily trap air. However, positive head pressure from the source container will cause the one-way valve to open to purge air during the ejection or pump-out portion of the peristaltic or shuttle pump stroke. Placing the airtrap downstream of the pump has the advantages of removing air as a final check before delivery to the patient and readily eliminating air because the line tends to be always in a state of positive pressure. The airtrap may be placed at a machine end of the drug delivery line, so that the airtrap may be clipped removeably to or grabbed removeably by the drug delivery machine.

In light of the disclosure herein and without limiting the disclosure in any way, in a first aspect of the present disclosure, which may be combined with any other aspect listed herein unless specified otherwise, an airtrap for a medical or physiological fluid includes: a conical housing having a radius that increases from its top to its bottom when the housing is positioned for operation; a medical or physiological fluid inlet located at an upper portion of the conical housing; a medical or physiological fluid outlet located at a lower portion of the conical housing, the inlet and the outlet positioned and arranged so that medical or physiological fluid spirals in an increasing arc around an inside of the conical housing downwardly from the inlet to the outlet; and a gas collection area located at the upper portion of the conical housing.

In a second aspect of the present disclosure, which may be combined with any other aspect listed herein unless specified otherwise, the airtrap includes a gas release valve located at an opening in the upper portion of the conical housing.

In a third aspect of the present disclosure, which may be combined with the second aspect in combination with any other aspect listed herein unless specified otherwise, the gas release valve is a check valve.

In a fourth aspect of the present disclosure, which may be combined with the second aspect in combination with any other aspect listed herein unless specified otherwise, the gas release valve includes a seal that stretches to open under gas pressure and self-closes once the gas pressure is released.

In a fifth aspect of the present disclosure, which may be combined with any other aspect listed herein unless specified otherwise, the airtrap includes a hydrophobic membrane located beneath an opening in the upper portion of the conical housing.

In a sixth aspect of the present disclosure, which may be combined with any other aspect listed herein unless specified otherwise, the medical or physiological fluid inlet is at least substantially horizontally disposed when the airtrap is positioned for operation.

In a seventh aspect of the present disclosure, which may be combined with any other aspect listed herein unless specified otherwise, the medical or physiological fluid outlet is at least substantially horizontally disposed when the airtrap is positioned for operation.

In an eighth aspect of the present disclosure, which may be combined with any other aspect listed herein unless specified otherwise, the top of the conical housing at the upper portion is flat and defines a gas release outlet.

In a ninth aspect of the present disclosure, which may be combined with any other aspect listed herein unless specified otherwise, a bottom wall of the conical housing at the lower portion of the conical housing rises within an outer conical wall of the conical housing.

In a tenth aspect of the present disclosure, which may be combined with the ninth aspect in combination with any other aspect listed herein unless specified otherwise, the rising bottom wall forms an inner conical wall inside of the outer conical wall.

In an eleventh aspect of the present disclosure, which may be combined with the ninth aspect in combination with any other aspect listed herein unless specified otherwise, the rising bottom wall helps the medical or physiological fluid to spiral around the inside of the conical housing.

In a twelfth aspect of the present disclosure, which may be combined with any other aspect listed herein unless specified otherwise, the gas collection area is located at an upper, central portion of the conical housing.

In a thirteenth aspect of the present disclosure, which may be combined with any other aspect listed herein unless specified otherwise, the airtrap includes structure for being mounted in its position for operation.

In a fourteenth aspect of the present disclosure, which may be combined with any other aspect listed herein unless specified otherwise, a renal therapy blood treatment system includes: a blood pump; and a blood set for operation with the blood pump, the blood set having an airtrap including a conical housing having a radius that increases from its top to its bottom when the housing is positioned for operation, a blood inlet located at an upper portion of the conical housing, a blood outlet located at a lower portion of the conical housing, the inlet and the outlet positioned and arranged so that blood spirals around an inside of the conical housing downwardly from the inlet to the outlet, and a gas collection area located at an upper portion of the conical housing.

In a fifteenth aspect of the present disclosure, which may be combined with the fourteenth aspect in combination with any other aspect listed herein unless specified otherwise, the blood set includes an arterial line and a venous line, and wherein the airtrap is located in the venous line.

In a sixteenth aspect of the present disclosure, which may be combined with the fourteenth aspect in combination with any other aspect listed herein unless specified otherwise, the renal therapy blood treatment system includes a dialysis fluid circuit, the airtrap a first airtrap, and which includes at least one second conical airtrap located in the dialysis fluid circuit.

In a seventeenth aspect of the present disclosure, which may be combined with the fourteenth aspect in combination with any other aspect listed herein unless specified otherwise, the renal therapy blood treatment system includes a chassis housing the blood pump and including mounting features for removeably mounting the airtrap in its position for operation.

In an eighteenth aspect of the present disclosure, which may be combined with the fourteenth aspect in combination with any other aspect listed herein unless specified otherwise, the blood set is configured to be connected to a patient, and wherein the airtrap aims to prevent air from reaching the patient.

In a nineteenth aspect of the present disclosure, which may be combined with any other aspect listed herein unless specified otherwise, a peritoneal dialysis system includes: a peritoneal dialysis fluid pump; and a disposable cassette for operation with the peritoneal dialysis fluid pump, the disposable cassette in fluid communication with a patient line having an airtrap including a conical housing having a radius that increases from its top to its bottom when the housing is positioned for operation, a peritoneal dialysis fluid inlet located at an upper portion of the conical housing, a peritoneal dialysis fluid outlet located at a lower portion of the conical housing, the inlet and the outlet positioned and arranged so that peritoneal dialysis fluid spirals around an inside of the conical housing downwardly from the inlet to the outlet, and a gas collection area located at an upper portion of the conical housing.

In a twentieth aspect of the present disclosure, which may be combined with the nineteenth aspect in combination with any other aspect listed herein unless specified otherwise, the peritoneal dialysis system includes a chassis housing the peritoneal dialysis fluid pump and including mounting features for removeably mounting the airtrap in its position for operation.

In a twenty-first aspect of the present disclosure, which may be combined with the nineteenth aspect in combination with any other aspect listed herein unless specified otherwise, the patient line is configured to be connected to a patient, and wherein the airtrap aims to prevent air from reaching the patient.

In a twenty-second aspect of the present disclosure, which may be combined with any other aspect listed herein unless specified otherwise, an infusion pump system includes: a drug delivery pump; and a drug delivery set for operation with the drug delivery pump, the drug delivery set including a drug delivery line having an airtrap, the airtrap including a conical housing having a radius that increases from its top to its bottom when the housing is positioned for operation, an intravenous drug inlet located at an upper portion of the conical housing, an intravenous drug outlet located at a lower portion of the conical housing, the inlet and the outlet positioned and arranged so that an intravenous drug spirals around an inside of the conical housing downwardly from the inlet to the outlet, and a gas collection area located at an upper portion of the conical housing.

In a twenty-third aspect of the present disclosure, which may be combined with the twenty-second aspect in combination with any other aspect listed herein unless specified otherwise, the infusion pump system includes a chassis housing the drug delivery pump and including mounting features for removeably mounting the airtrap in its position for operation.

In a twenty-fourth aspect of the present disclosure, which may be combined with the twenty-second aspect in combination with any other aspect listed herein unless specified otherwise, the drug delivery line is configured to be connected to a patient, and wherein the airtrap aims to prevent air from reaching the patient.

In a twenty-fifth aspect of the present disclosure, which may be combined with any other aspect listed herein unless specified otherwise, an airtrap for a medical or physiological fluid includes: a head section having (i) a largest diameter extending perpendicular to a plane bisecting the airtrap or (ii) a largest width and height extending perpendicular to the plane bisecting the airtrap; a medical or physiological fluid inlet provided by the head section; a tubular tail section, which when the airtrap is mounted for operation extends downwardly from the head section, the tubular tail section smaller in (a) diameter or (b) largest cross-sectional distance than (i) the largest diameter of the head section or (ii) the largest width or height of the head section, the tubular tail section including at least one smooth curve, jog and/or undulation positioned and arranged to cause fluid flowing from the head section, through the tubular tail section, to change direction at least one time; and a medical or physiological fluid outlet located at a distal end of the tubular section, beneath the medical or physiological fluid inlet when the airtrap is mounted for operation, such that air rises to a top of the head section via buoyancy, and wherein the at least one smooth curve, jog and/or undulation helps to dislodge air from the medical or physiological fluid.

In a twenty-sixth aspect of the present disclosure, which may be combined with the twenty-fifth aspect in combination with any other aspect listed herein unless specified otherwise, the medical or physiological fluid outlet at the distal end of the tail section extends generally horizontally when the airtrap is mounted for operation.

In a twenty-seventh aspect of the present disclosure, which may be combined with the twenty-fifth aspect in combination with any other aspect listed herein unless specified otherwise, the medical or physiological fluid inlet provided by the head section extends generally horizontally when the airtrap is mounted for operation.

In a twenty-eighth aspect of the present disclosure, which may be combined with the twenty-fifth aspect in combination with any other aspect listed herein unless specified otherwise, the (a) diameter of the tubular tail section or (b) largest cross-sectional distance of the tail section narrows as it extends from the head section to the medical or physiological fluid outlet at the distal end of the tail section.

In a twenty-ninth aspect of the present disclosure, which may be combined with the twenty-fifth aspect in combination with any other aspect listed herein unless specified otherwise, the top of the head section includes an enlarged upper area for air collection.

In a thirtieth aspect of the present disclosure, which may be combined with the twenty-fifth aspect in combination with any other aspect listed herein unless specified otherwise, the airtrap includes a gas release valve located at an opening in the top of the head section.

In a thirty-first aspect of the present disclosure, which may be combined with the thirtieth aspect in combination with any other aspect listed herein unless specified otherwise, the gas release valve is a check valve.

In a thirty-second aspect of the present disclosure, which may be combined with the thirtieth aspect in combination with any other aspect listed herein unless specified otherwise, the gas release valve includes a seal that stretches to open under gas pressure and self-closes once the gas pressure is released.

In a thirty-third aspect of the present disclosure, which may be combined with the twenty-fifth aspect in combination with any other aspect listed herein unless specified otherwise, the airtrap includes a hydrophobic membrane located beneath the top of the head section.

In a thirty-fourth aspect of the present disclosure, which may be combined with the twenty-fifth aspect in combination with any other aspect listed herein unless specified otherwise, the airtrap includes a resealable septum located at an opening in the top of the head section.

In a thirty-fifth aspect of the present disclosure, which may be combined with the twenty-fifth aspect in combination with any other aspect listed herein unless specified otherwise, the airtrap is in the shape of a seahorse.

In a thirty-sixth aspect of the present disclosure, which may be combined with the twenty-fifth aspect in combination with any other aspect listed herein unless specified otherwise, the airtrap is provided in a blood set for operation with a blood pump.

In a thirty-seventh aspect of the present disclosure, which may be combined with the twenty-fifth aspect in combination with any other aspect listed herein unless specified otherwise, the airtrap is provided in a venous line of the blood set.

In a thirty-eighth aspect of the present disclosure, which may be combined with the twenty-fifth aspect in combination with any other aspect listed herein unless specified otherwise, the airtrap is provided in a patient line in fluid communication with a disposable cassette for operation with a dialysis fluid pump.

In a thirty-ninth aspect of the present disclosure, which may be combined with the twenty-fifth aspect in combination with any other aspect listed herein unless specified otherwise, the airtrap is provided in a drug delivery line of a drug delivery set for operation with the drug delivery pump.

In a fortieth aspect of the present disclosure, which may be combined with any other aspect listed herein unless specified otherwise, an airtrap for a medical or physiological fluid includes: a conical housing having a radius that decreases from its top to its bottom when the housing is positioned for operation; a medical or physiological fluid inlet located at an upper portion of the conical housing; a medical or physiological fluid outlet located at a lower portion of the conical housing, the inlet and the outlet positioned and arranged so that medical or physiological fluid spirals in a decreasing arc around an inside of the conical housing downwardly from the inlet to the outlet; and a gas collection area located at the upper portion of the conical housing.

In a forty-first aspect of the present disclosure, which may be combined with the fortieth aspect in combination with any other aspect listed herein unless specified otherwise, the airtrap has a toroidal top leading to an inner cone.

In a forty-second aspect of the present disclosure, any of the structure and functionality disclosed in connection with FIGS. 1 to 11 may be combined with any of the other structure and functionality disclosed in connection with FIGS. 1 to 11.

In light of the present disclosure and the above aspects, it is therefore an advantage of the present disclosure to provide an improved air removal device, system and method for renal failure therapies.

It is another advantage of the present disclosure to provide an improved air removal device, system and method for intravenous drug delivery treatments.

It is a further advantage of the present disclosure to provide an air removal device, system and method that is efficient in trapping air bubbles from blood or medical fluid flow.

It is still another advantage of the present disclosure to provide an air removal device, system and method in which trapped air can be removed from the system, minimizing gas storage space needed.

It is still a further advantage of the present disclosure to provide an air removal device, system and method that minimizes blood compliment activation and propensity to cause clotting, which tends to avoid blood recirculation, stagnation and high shear.

It is yet another advantage of the present disclosure to provide an air removal device, system and method that may be primed, rinsed and/or washed for reuse.

It is yet a further advantage of the present disclosure to provide an air removal device, system and method that uses materials of construction that are blood and/or medical fluid compatible and remain durable when sterilized and/or disinfected.

Further still, it is an advantage of the present disclosure to provide an air removal device, system and method that may reduce the risk of infusing large air boluses (e.g., >~0.5 ml in volume), bubbles (e.g., ~1 µL to ~500 µL in volume), and microbubbles (e.g., <~1 µL in volume).

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Hardware

The examples described herein are applicable to any medical fluid therapy system that delivers a medical fluid, such as a blood, dialysis fluid, substitution fluid or intravenous drug delivery. The examples are particularly well suited for kidney failure therapies, such as all forms of hemodialysis ("HD"), hemofiltration ("HF"), hemodiafiltration ("HDF") and continuous renal replacement therapies ("CRRT"), referred to herein collectively or generally individually as renal failure therapy. Moreover, the machines and any of the airtraps herein may be used in clinical or home settings. For example, the machine and any one or more of the airtraps may be employed in an in-center HD machine, which runs virtually continuously throughout the day. Alternative, they may be used in a home HD machine, which can for example be run at night while the patient is sleeping. Moreover, each of the renal failure therapy examples described herein may include a diffusion membrane or filter, such as a dialyzer, e.g., for HD or HDF, or a hemofilter, e.g., for HF.

Figure 1:
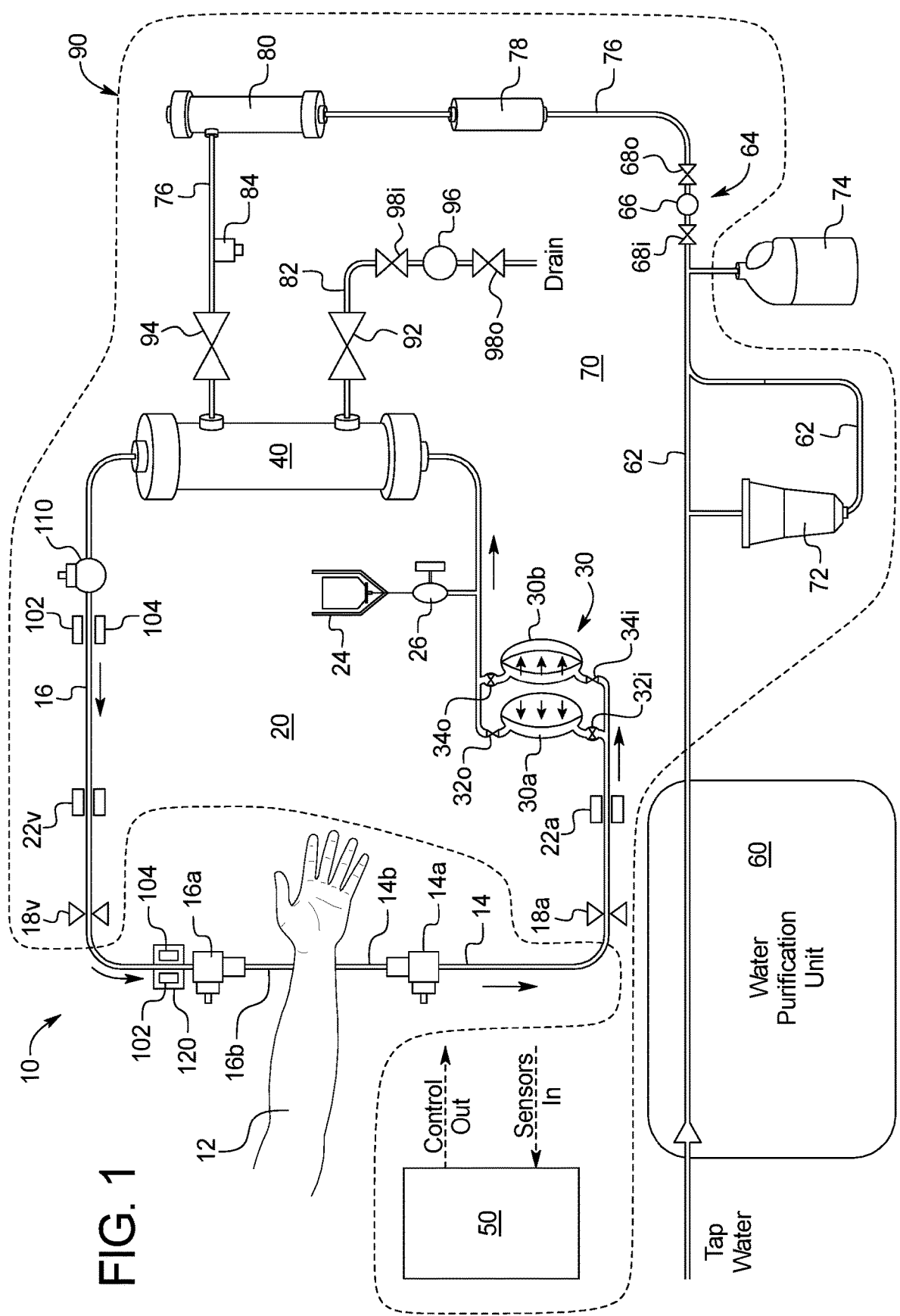
FIG. 1 is a schematic illustration of one embodiment of a renal failure therapy employing any of the air removal devices, systems or methods of the present disclosure.

Referring now to FIG. 1, one embodiment for a renal failure therapy system 10 employing any of the airtraps and associated methodology described herein is illustrated using an HD machine. Generally, system 10 is shown having a very simplified version of the dialysis fluid or process fluid delivery circuit. The blood circuit is also simplified but not to the degree that the dialysis fluid circuit is simplified. It should be appreciated that the circuits have been simplified to make the description of the present disclosure easier, and that the systems if implemented would have additional structure and functionality, such as is found in the publications incorporated by reference above.

System 10 of FIG. 1 includes a blood circuit 20. Blood circuit 20 pulls blood from and returns blood to a patient 12.

Blood is pulled from patient 12 via an arterial line 14, and is returned to the patient via a venous line 16. Arterial line 14 includes an arterial line connector 14*a* that connects to an arterial needle 14*b*, which is in blood draw flow communication with patient 12. Venous line 16 includes a venous line connector 16*a* that connects to a venous needle 16*b*, which is in blood return flow communication with the patient. Arterial and venous lines 14 and 16 also include line clamps 18*a* and 18*v*, which can be spring-loaded, fail-safe mechanical pinch clamps. Line clamps 18*a* and 18*v* are closed automatically in an emergency situation in one embodiment.

Arterial and venous lines 14 and 16 also include air or bubble detectors 22*a* and 22*v*, respectively, which can be ultrasonic air detectors. Air or bubble detectors 20*a* and 20*v* look for air in the arterial and venous lines 14 and 16, respectively. If air is detected by one of air detectors 22*a* and 22*v*, system 10 closes line clamps 18*a* and 18*v*, pauses the blood and dialysis fluid pumps, and provides instructions to the patient to clear the air so that treatment can resume.

A blood pump 30 is located in arterial line 14 in the illustrated embodiment. In the illustrated embodiment, blood pump 30 includes a first blood pump pod 30*a* and a second blood pump pod 30*b*. Blood pump pod 30*a* operates with an inlet valve 32*i* and an outlet valve 32*o*. Blood pump pod 30*b* operates with an inlet valve 34*i* and an outlet valve 34*o*. In an embodiment, blood pump pods 30*a* and 30*b* are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure. Blood pump 30 is alternatively a peristaltic pump operating with the arterial line 14 tube.

A heparin vial 24 and heparin pump 26 are located between blood pump 30 and blood filter 40 (e.g., dialyzer) in the illustrated embodiment. Heparin pump 26 can be a pneumatic pump or a syringe pump (e.g., stepper motor driven syringe pump). Supplying heparin upstream of blood filter 40 helps to prevent clotting of the blood filter membranes.

A control unit 50 includes one or more processor and memory. Control unit 50 receives air detection signals from air detectors 22*a* and 22*v* (and other sensors of system 10, such as temperature sensors, blood leak detectors, conductivity sensors, pressure sensors, and access disconnection transducers 102, 104), and controls components such as line clamps 18*a* and 18*v*, blood pump 30, heparin pump 26, and the dialysis fluid pumps.

Blood exiting blood filter 40 via venous line 16 flows through an airtrap 110 (referring collectively or generally individually to any of airtraps 110*a* to 110*c* discussed below). Airtrap 110 removes air from the blood before the dialyzed blood is returned to patient 12 via venous line 16 as discussed in detail below.

With the hemodialysis version of system 10 of FIG. 1, dialysis fluid or dialysate is pumped along the outside of the membranes of blood filter 40, while blood is pumped through the insides of the blood filter membranes. Dialysis fluid or dialysate is prepared beginning with the purification of water via a water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structure to purify tap water (e.g., remove pathogens and ions such as chlorine) so that the water is in one implementation below 0.03 endotoxin units/ml ("EU/ml") and below 0.1 colony forming units/ml ("CFU/ml"). Water purification unit 60 can be provided in a housing separate from the housing of the hemodialysis machine, which includes blood circuit 20 and a dialysis fluid circuit 70.

Dialysis fluid circuit 70 is again highly simplified in FIG. 1 to ease illustration and to better highlight blood circuit 20. Dialysis fluid circuit 70 in actuality may include all of the relevant structure and functionality set forth in the publications incorporated by reference above. Certain features of dialysis fluid circuit 70 are illustrated in FIG. 1. In the illustrated embodiment, dialysis fluid circuit 70 includes a to-blood filter dialysis fluid pump 64. Pump 64 is in one embodiment configured the same a blood pump 30. Pump 64, like pump 30, includes a pair of pump pods, which again may be spherically configured. The two pump pods, like with blood pump 30, are operated alternatingly so that one pump pod is filling with HD dialysis fluid, while the other pump pod is expelling HD dialysis fluid.

Pump 64 is a to-blood filter dialysis fluid pump. There is another dual pod pump 96, like pump 64, located in drain line 82 to push used dialysis fluid to drain. There is a third pod pump (not illustrated) for pumping pump purified water through a bicarbonate cartridge 72. There is a fourth pod pump (not illustrated) used to pump acid from acid container 74 into mixing line 62. The third and fourth pumps, the concentrate pumps, can be single pod pumps because continuous pumping is not as important in mixing line 62 because there is a buffering dialysis fluid tank (not illustrated) between mixing line 62 and to-blood filter dialysis fluid pump 64 in one embodiment.

A fifth pod pump (not illustrated) provided in drain line 82 is used to remove a known amount of ultrafiltration ("UF") when the HD therapy is provided. System 10 keeps track of the UF pump to control and know how much ultrafiltrate has been removed from the patient. System 10 ensures that the necessary amount of ultrafiltrate is removed from the patient by the end of treatment.

Each of the above-described pumps may alternatively be a peristaltic pump operating with a tube.

In one embodiment, purified water from water purification unit 60 is pumped along mixing line 62 though bicarbonate cartridge 72. Acid from container 74 is pumped along mixing line 62 into the bicarbonated water flowing from bicarbonate cartridge 72 to form an electrolytically and physiologically compatible dialysis fluid solution. The pumps and temperature-compensated conductivity sensors used to properly mix the purified water with the bicarbonate and acid are not illustrated but are disclosed in detail in the publications incorporated by reference above.

FIG. 1 also illustrates that dialysis fluid is pumped along a fresh dialysis fluid line 76, through a heater 78 and an ultrafilter 80, before reaching blood filter 40, after which the used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering bugs or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 will further include a blood leak detector (not illustrated but used to detect if a blood filter 40 fiber is torn) and other components that are not illustrated, such as balance chambers, plural valves, and a dialysis fluid holding tank, all illustrated and described in detail in the publications incorporated by reference above.

In the illustrated embodiment, hemodialysis system 10 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 may be reused. In one implementation, blood circuit 20 including blood filter 40 is hot water disinfected and reused daily for about one month, while dialysis fluid circuit 70 is hot water disinfected and reused for about six months.

In alternative embodiments, or for CRRT for example, multiple bags of sterilized dialysis fluid or infusate are ganged together and used one after another. In such a case, the emptied supply bags can serve as drain or spent fluid bags.

The machine 90 of system 10 includes an enclosure as indicated by the dotted line of FIG. 1. The enclosure of machine 90 varies depending upon the type of treatment, whether the treatment is in-center or a home treatment, and whether the dialysis fluid/infusate supply is a batch-type (e.g., bagged) or on-line. Although not illustrated in FIG. 1, the front of the enclosure of machine 90 may have structures configured to releasably clamp any of the airtraps 110 discussed herein in place and in their appointed configurations. For example, the conical airtrap 110a that narrows as it extends from bottom to top can be slid horizontally into a triangular bracket that extends from the front of the enclosure of machine 90, which holds conical airtrap 110a releasably upright in its proper operating position. On the other hand, the conical airtrap 110b that narrows as it extends from top to bottom can be slid downwardly into fork-like structures that extend from the front of the enclosure of machine 90, which holds conical airtrap 110b releasably upright in its proper operating position. Seahorse airtrap 110c can be held releasably in place via plural spring clips that extend from the front of the enclosure of machine 90.

Figure 2:
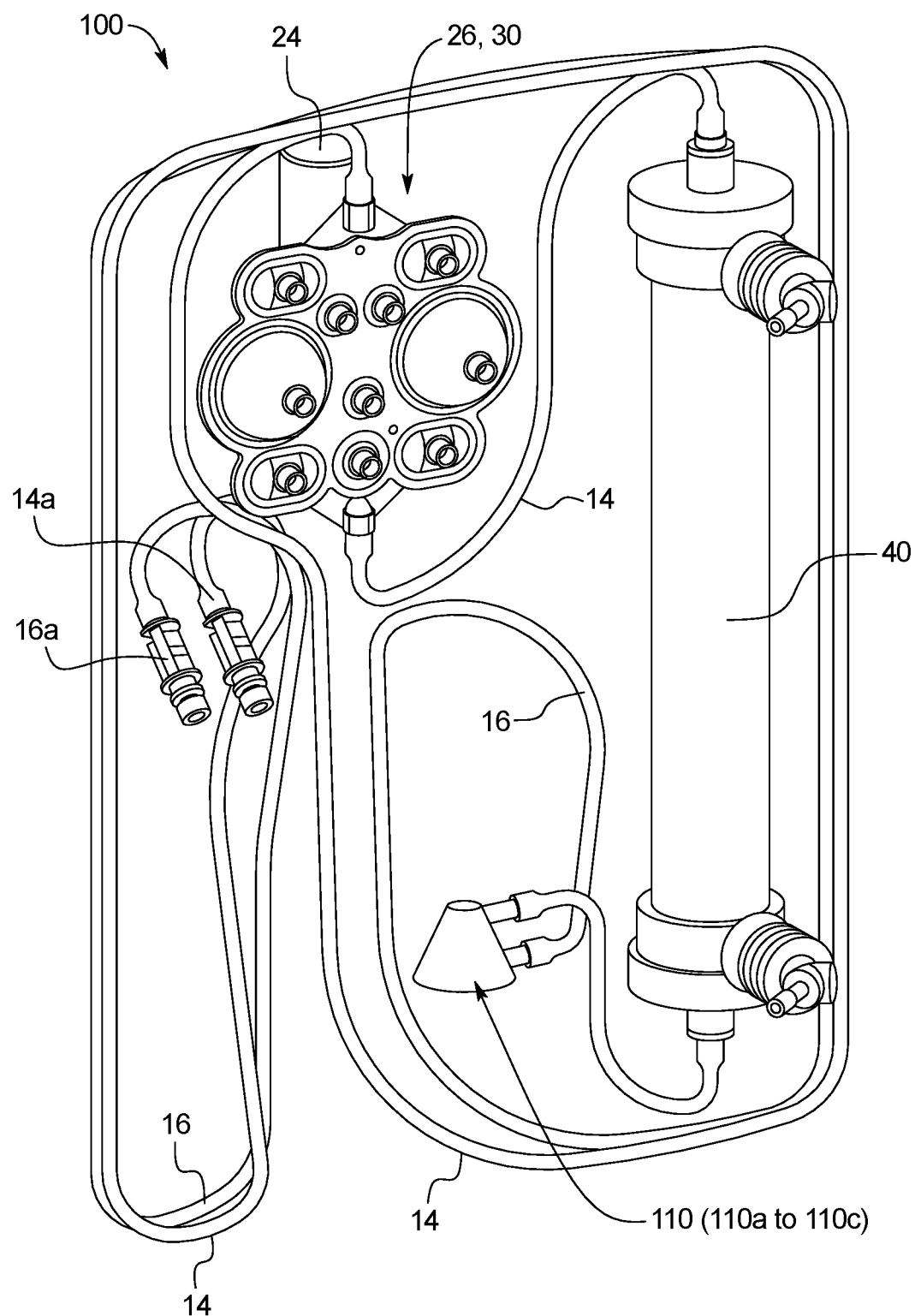
FIG. 2 is a perspective view illustrating any of the airtraps described herein operating with a blood set for use with a blood treatment machine.

FIG. 2 illustrates that machine 90 of system 10 of FIG. 1 may operate with a blood set 100. Blood set 100 includes arterial line 14, venous line 16, heparin vial 24 and heparin pump 26/blood pump 30 and blood filter 40 (e.g., dialyzer). Any of the airtraps 110 discussed herein may be located in venous line 16 to remove air from the blood before being returned to patient 12. Alternatively or additionally, any of the airtraps 110 discussed herein may be located in arterial line 14, e.g., between blood pump 30 and blood filter 40 (e.g., dialyzer), so as to receive blood under positive pressure. Further alternatively or additionally, any of the airtraps 110 discussed herein may be located in dialysate circuit, in mixing line 62 and/or fresh dialysis fluid line 76 to improve mixing accuracy and/or to remove air from fresh dialysis fluid line before reaching filter or dialyzer 40.

Airtraps

Figure 3:
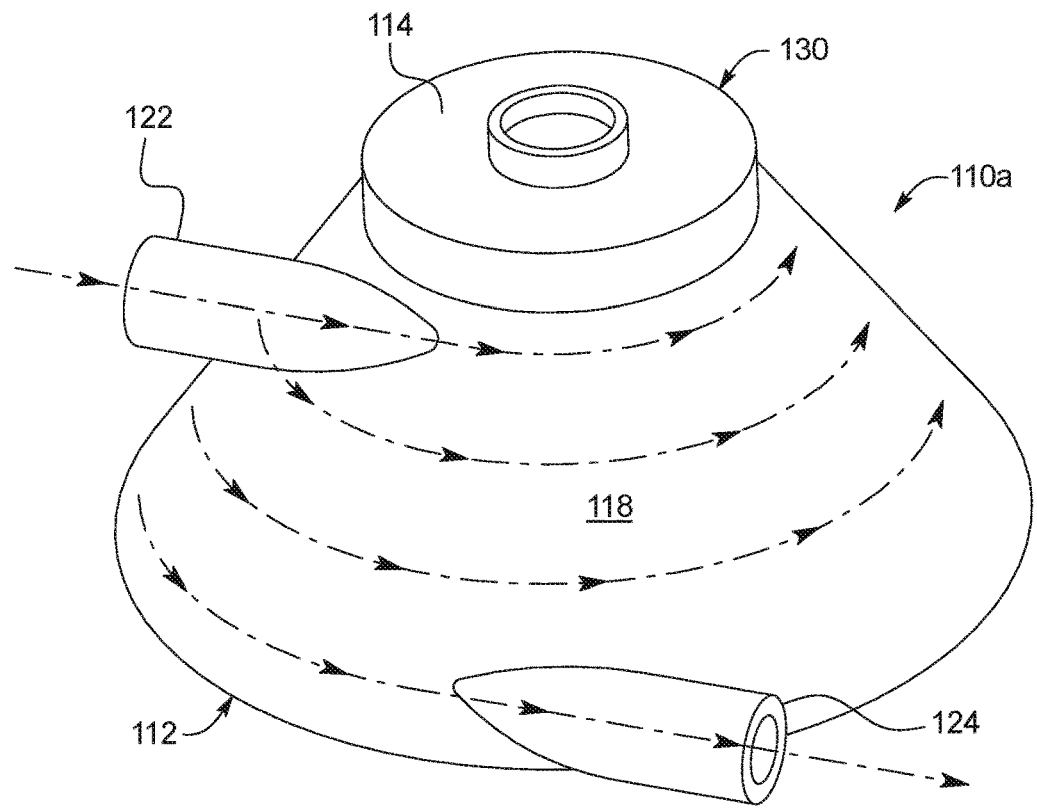
FIG. 3 is a perspective view of one embodiment of an airtrap of the present disclosure.
Figure 4:
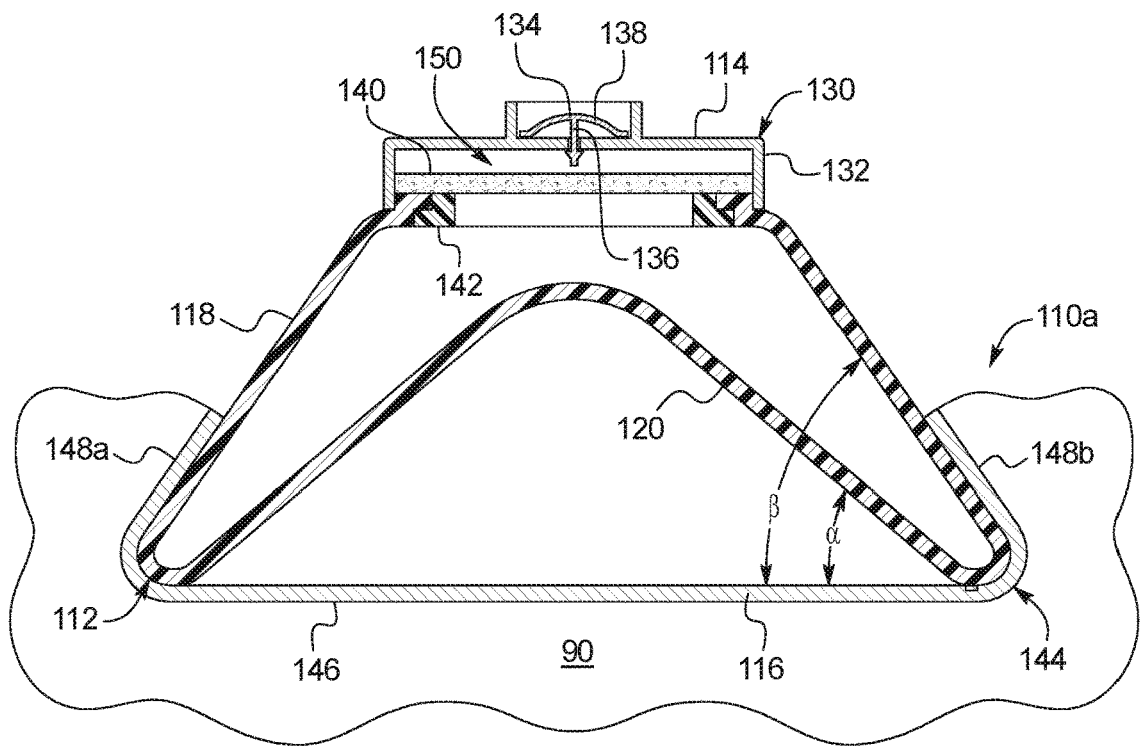
FIG. 4 is an cross-sectional elevation view of the airtrap embodiment of FIG. 3.

Referring now to FIGS. 3 and 4, one embodiment of an airtrap of the present disclosure is illustrated by airtrap 110a. Airtrap 110a includes a conical housing 112 that can be made of any medically acceptable material safe for contact with medical, biological or physiological fluid, such as blood, dialysis fluid, replacement or substitution fluid, or intravenous drug. Such materials include medically safe plastics or metals, such as silicone, polyvinylidene fluoride or polyvinylidene difluoride ("PVDF"), polysulfone, Kynar, silicone-based or silicone-coated materials, medical grade stainless steel, titanium and combinations thereof.

Conical housing 112 includes a top 114, bottom 116, outer conical wall 118, inner conical wall 120, inlet 122 and outlet 124. Inlet 122 and outlet 124 may have any suitable connections for connection to a medic fluid tube or pipe, such as compression connections, hose barb connections, threaded connections, luer lock connections and the like. Inlet 122 and outlet 124 are at least substantially horizontal when airtrap 110a is mounted in its operating position. Inlet 122 feeds into an upper portion, near the top 114 of conical housing 112. Outlet 124 extends from a lower portion, near the bottom 116 of conical housing 112. As illustrated, outer conical wall 118 increases in diameter as it extends from top 114 to bottom 116, therefore, outlet 124 resides further radially outwardly from a central axis of housing 112 than does inlet 122.

Inner conical wall 120 extends up from the bottom 116 of conical housing inside of outer conical wall 118. Inner conical wall 120 may strike a lesser angle (a) relative to horizontal (e.g., 15 to 35 degrees) than does an angle ((3) of outer conical wall 118 (e.g., 40 to 70 degrees). The gap between inner conical wall 120 and outer conical wall 118 forms the fluid/gas separation chamber for airtrap 110a. This chamber may have a volume from about ten $cm^3$ to about twenty $cm^3$.

Inner conical wall 120 and outer conical wall 118 along with the orientation and placement of inlet 122 and 124 cause any of the fluids described herein to spin from the top portion of housing 112 to the bottom portion of housing 112 in an increasing arc (as indicated by dash-dot arrows). The spinning centripetally causes heavier fluid to migrate towards outer conical wall 118 and lighter gas or air to separate and migrate towards inner conical wall 120. Air or gas moves buoyantly centrally up along inner conical wall 120 to the central top 114 of housing 112 in gas collection area 150.

Central top 114 of housing 112 of airtrap 110a may have any one of multiple configurations. In one embodiment, top 114 is a solid structure, wherein released air or gas remains trapped at the central top 114 of housing 112 over one or more treatment, or one or more cycles of a single treatment, after which airtrap 110a is discarded. In a manual air removal embodiment, central top 114 of housing 112 includes a septum (not illustrated) that may be sealingly pierced by a sterile needle to remove air during or after a treatment. Here, airtrap 110a, may be reused over multiple treatments. In an automatic air removal embodiment, central top 114 of housing 112 is placed in valved connection with an air line and air pump (not illustrated), which under control of control unit 50 automatically pulls air from housing 112 at desired intervals. Here again, airtrap 110a, may be reused over multiple treatments.

In the illustrated embodiment, central top 114 of housing 112 of airtrap 110a includes a passive air removal structure, which includes a one-way or check gas release valve assembly 130. One-way or check gas release valve assembly 130 includes a valve housing 132 holding a flexible valve 134. Flexible valve 134 may be silicone or any of the flexible materials discussed herein. Flexible valve 134 may include a stem 136 that is crimped to valve housing 132 and a valve seat 138 formed with or attached to valve stem 136. Stem 136 is held under tension against valve housing 132, so as to pull valve seat 138 sealingly against valve housing 132, closing valve assembly 130 and trapping gas or air within airtrap housing 112. Gas or air under pressure within airtrap housing 112 pushes against valve seat 138, tending to open the valve seat. When the gas or air pressure builds to a predefined level, e.g., 100 to 300 mmHg, valve seat 138 becomes unseated from valve housing 132, allowing gas or air to burp out of airtrap 110a, relieving gas or air pressure.

Once pressure is relieved, stem 136 pulls seat 138 self-sealingly back against valve housing 132. This burping or purging cycle may be repeated one or more time during a single or multiple treatments.

In the illustrated embodiment, as part of or in addition to valve assembly 130, a hydrophobic filter 140 (air passing but liquid retaining), e.g., in the form of a circular wafer, may be placed beneath valve stem 136 and valve seat 138 to prevent liquid or fluid within housing 112 from escaping airtrap 110a when valve assembly 130 is burped as described previously. Hydrophobic filter 140 in an embodiment is made of polyvinylidene fluoride or polyvinylidene difluoride ("PVDF"). Hydrophobic filter 140 may be held in place against airtrap housing 112 or valve housing 132 via a polysulfone or other material fixing ring 142, which may be welded to, formed with, adhered or attached to airtrap housing 112 or valve housing 132.

FIG. 4 also illustrates that airtrap 110a may be held removeably in place via a bracket 144 that extends from the chassis of machine 90. Bracket 144 may be formed integrally with the front panel of machine 90 (e.g., part of a molded plastic front panel) or be attached to the front panel. In the illustrated embodiment, bracket 144 is triangular shaped, including a horizontal bottom wall 146 and angled arms 148a and 148b extending up from bottom wall 146 at an angle coinciding with the angle of outer conical wall 118 (e.g., 40 to 70 degrees). Angled arms 148a and 148b do not extend fully to form a complete triangle and instead stop to allow for the at least substantially flat top 114 of airtrap 110a. Bracket 144 extends a distance from the front panel of machine 90 sufficient to hold airtrap 110a firmly in place, however, the bracket stops short of inlet 122 and outlet 124, so as to allow tubes (not illustrated) to run freely to and from the inlet and outlet, respectively. Bracket 144 as illustrated holds airtrap 110a in its proper position for operation. Bracket 144 also allows for the ready insertion and removal of airtrap 110a.

The housings of both airtraps 110a and 110b may also include smooth fluid contacting surfaces to reduce or prevent eddy currents.

Figure 5:
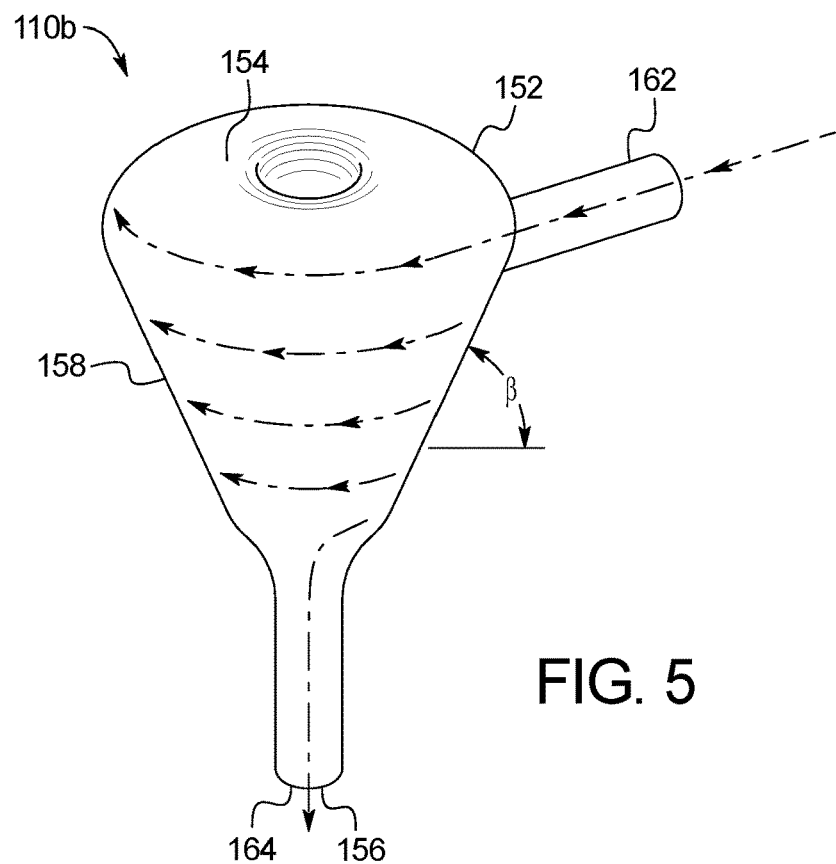
FIG. 5 is a solid perspective view of a second embodiment of an airtrap of the present disclosure.
Figure 6:
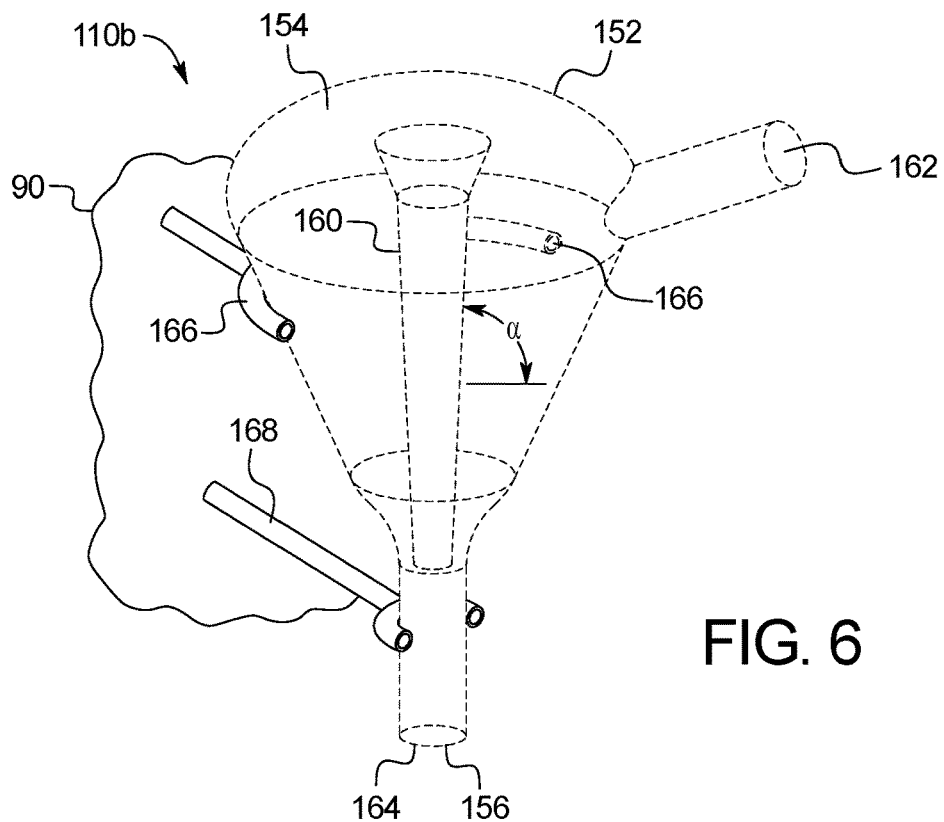
FIG. 6 is a see-through perspective view of the second embodiment of the airtrap of FIG. 5.

Referring now to FIGS. 5 and 6, another embodiment of an airtrap of the present disclosure is illustrated by airtrap 110b. Airtrap 110b again includes a conical housing 152 that may be made of any medically acceptable material safe for contact with medical, biological or physiological fluid, such as blood, dialysis fluid, replacement or substitution fluid, or intravenous drug. Such materials include medically safe plastics or metals, such as silicone, polyvinylidene fluoride or polyvinylidene difluoride ("PVDF"), polysulfone, Kynar, silicone-based or silicone-coated materials, medical grade stainless steel, titanium and combinations thereof.

Conical housing 152 in the illustrated embodiment includes a toroidal top 154, bottom 156, outer conical wall 158, inner conical wall or cone 160, inlet 162 and outlet 164. Inlet 162 and outlet 164 may have any suitable connections for connection to a medic fluid tube or pipe, such as compression connections, hose barb connections, threaded connections, luer lock connections and the like. Inlet 162 is at least substantially horizontal when airtrap 110b is mounted in its operating position. Inlet 162 feeds into an upper portion, near the top 154 of conical housing 152. Outlet 164 in the illustrated embodiment extends vertically downwardly from a lower portion, at or near the bottom 156 of conical housing 152. As illustrated, outer conical wall 158 in this embodiment decreases in diameter as it extends from top 154 to bottom 156, therefore, inlet 162 resides further radially outwardly from a central axis of housing 112 than does outlet 164, which as illustrated can reside along the central axis.

Inner conical wall or cone 160 extends down from the top 154 of conical housing 152 inside of outer conical wall 158. Inner conical wall 160 may strike a greater angle ($\alpha$) relative to horizontal (e.g., 60 to 88 degrees) than does an angle ($\beta$) of outer conical wall 158 (e.g., 40 to 70 degrees). The gap between inner conical wall or cone 160 and outer conical wall 158 forms the fluid/gas separation chamber for airtrap 110b. This chamber may have a volume from about eight cm$^3$ to about eighteen cm$^3$.

Inner conical wall or cone 160 and outer conical wall 158 along with the orientation and placement of inlet 162 and outlet 164 cause any of the fluids described herein to spin from the top portion of housing 152 to the bottom portion of housing 152 in a decreasing arc (as indicated by dash-dot arrows). The fluid spinning centripetally causes heavier fluid to migrate towards outer conical wall 158 and lighter gas or air to separate and migrate towards inner conical wall or cone 160. Air or gas moves buoyantly centrally up along inner conical wall or cone 160 to the peripheral top 154 of housing 152.

The periphery of toroidal composite top 154 of housing 152 of airtrap 110b may have any of the air trapping, manual air removal, active air removal or passive air removal configurations described above for airtrap 110a.

FIG. 6 also illustrates that airtrap 110b may be held removeably in place via a pair of fork-like structures 166 and 168 that extend from the chassis of machine 90. Fork-like structures 166 and 168 may be formed integrally with the front panel of machine 90 (e.g., part of a molded plastic front panel) or be attached to the front panel. In the illustrated embodiment, fork-like structure 166 is wider in diameter and sized to releasably capture an upper portion of housing 152 of airtrap 110b, while fork-like structure 168 is narrower in diameter and sized to releasably capture, e.g., snap-fit to, a lower portion of housing 152. Lower fork-like structure 168 may for example snap-fit to a fixed diameter tube of outlet 164. Fork-like structures 166 and 168 extend a distance from the front panel of machine 90 sufficient to hold airtrap 110b firmly in place, without tilting, and to allow tubes (not illustrated) to run freely to and from the inlet 162 and outlet 164, respectively. Fork-like structures 166 and 168 as illustrated hold airtrap 110b in its proper position for operation. Fork-like structures 166 and 168 also allow for the ready insertion and removal of airtrap 110b.

Figure 7:
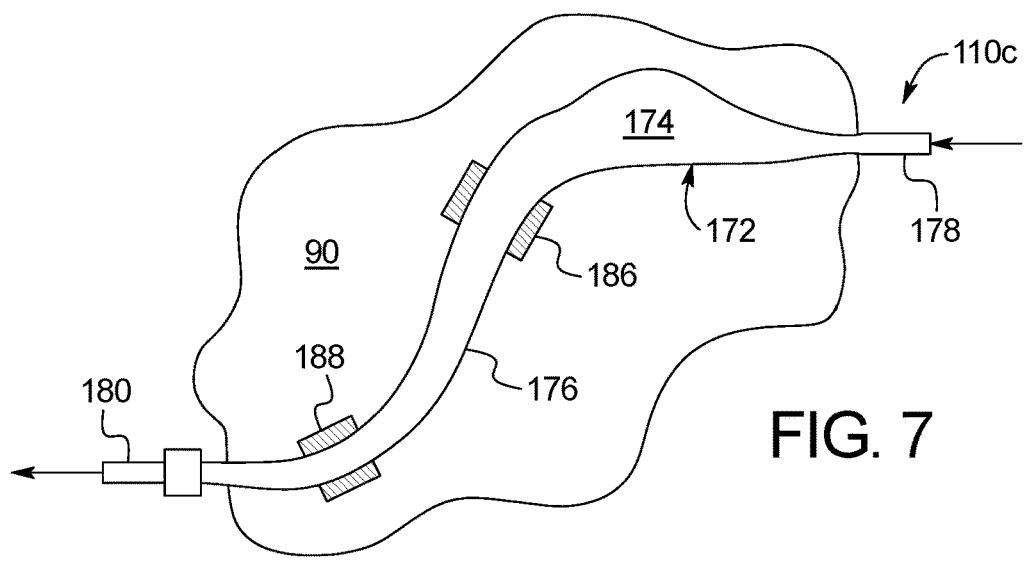
FIG. 7 is a side elevation view of a third embodiment of an airtrap of the present disclosure.
Figure 8:
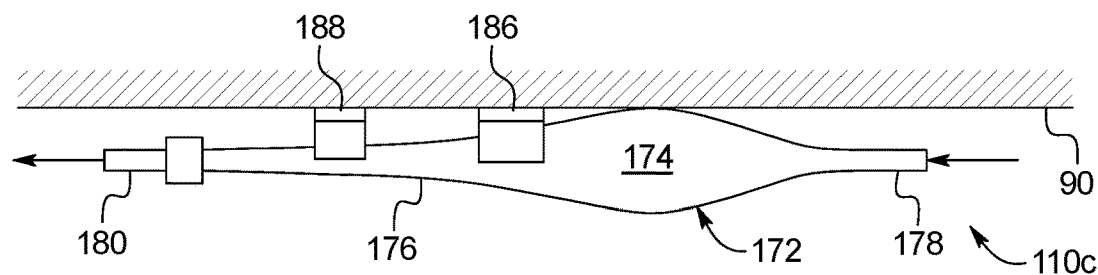
FIG. 8 is a top view of the third embodiment of the airtrap of FIG. 7.
Figure 9:
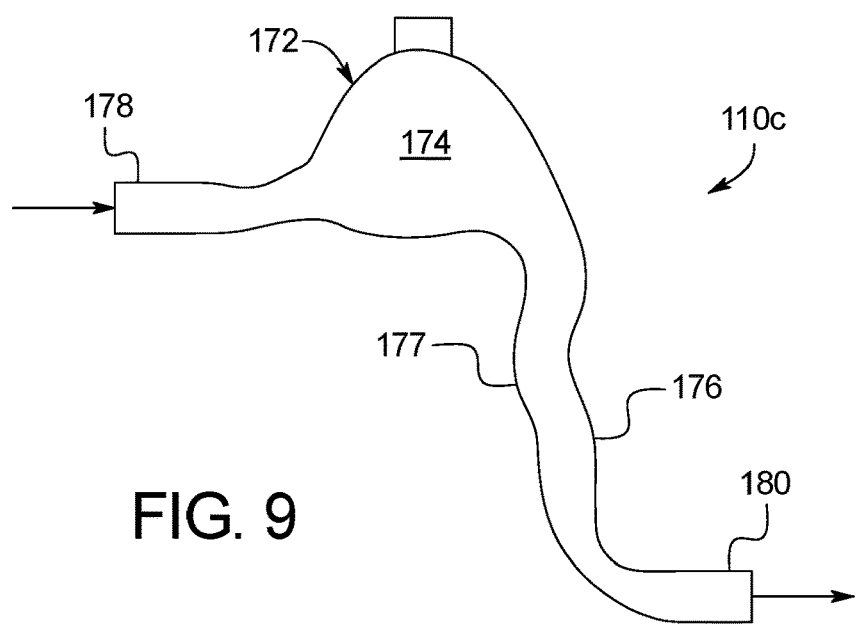
FIG. 9 is a side elevation view of a modified third embodiment of the airtrap of the present disclosure.

Referring now to FIGS. 7 to 9, a further embodiment of an airtrap of the present disclosure is illustrated by airtrap 110c. Airtrap 110c includes a seahorse-shaped housing 172, which may be made of any medically acceptable material safe for contact with medical, biological or physiological fluid, such as blood, dialysis fluid, replacement or substitution fluid, or intravenous drug. Such materials again include medically safe plastics or metals, such as silicone, polyvinylidene fluoride or polyvinylidene difluoride ("PVDF"), polysulfone, Kynar, silicone-based or silicone-coated materials, medical grade stainless steel, titanium and combinations thereof.

Seahorse-shaped housing 172 includes a head section 174 and a tail section 176 extending from head section 174. Tail section 176 may be curved, straight, have jogs and/or undulations 177 as desired. Head section 174 forms an inlet 178, while the distal end of tail section 176 forms and outlet 180. Inlet 178 and outlet 180 may have any suitable connections for connection to a medic fluid tube or pipe, such as compression connections, hose barb connections, threaded connections, luer lock connections and the like. Inlet 178 is at least substantially horizontal when airtrap 110b is mounted in its operating position. Inlet 178 feeds into head section 174, near the top of seahorse-shaped housing 172. Outlet 180 in the illustrated embodiment also extends at least substantially horizontally at the bottom of tail section 176.

Head section 174 in an embodiment (i) if rounded includes a largest diameter extending perpendicular to a plane bisecting airtrap 110b or (ii) if non-rounded (e.g., rectangular or square shape) includes a largest width and height extending perpendicular to the plane bisecting the airtrap. Tubular tail section 176 is structured in an embodiment such that when airtrap 110c is mounted for operation, tail section 176 extends downwardly from head section 174, and wherein tubular tail section 176 (a) if circular in cross-section is smaller in diameter or (b) if non-circular in cross-section is smaller in its largest cross-sectional distance than (i) the largest diameter of the head section or (ii) the largest width and height of the head section.

The head section 174 may form an enlarged hump before gradually narrowing as directed through tail section 176 downward to outlet 180. Head section 174, tail section 176, inlet 178 and outlet 180 may be constructed, positioned and arranged so that medical or physiological fluid flow initially expands and slows, separating and storing air in head section 174, while thereafter gradually accelerating from inlet 178 to outlet 180.

Airtrap 110c relies mainly on buoyancy forces to all air or gas to separate from whatever fluid is flowing through the airtrap. Tail section 176 provides a relatively long and at least somewhat vertical length, providing time and opportunity for air or gas to bubble up to head section 174. FIG. 9 illustrates that head section 174 may be larger to hold more air or gas. The internal volume of seahorse-shaped housing 172 may be about seven $cm^3$ to about seventeen $cm^3$. Tail section 176 may be curved, have jogs and/or undulations 177 to change the direction of fluid flowing through airtrap 110b and to help separate the bubbles from the liquid.

The top of head section 174 of housing 172 of airtrap 110b may have any of the air trapping, manual air removal, active air removal or passive air removal configurations described above for airtrap 110a.

FIGS. 7 and 8 also illustrate that airtrap 110c may be held removeably in place via a pair of spring clips 186 and 188 that extend from the chassis of machine 90. Spring clips 186 and 188 may be formed integrally with the front panel of machine 90 (e.g., part of a molded plastic front panel) or be attached to the front panel. In the illustrated embodiment, spring clip 186 is wider and sized to releasably capture an upper portion of tail section 176 of housing 172 of airtrap 110c, while spring clip 188 is narrower and sized to releasably capture a lower portion of the tail section. Spring clips 186 and 188 extend a distance from the front panel of machine 90 sufficient to hold airtrap 110b firmly in place, without tilting, and to allow tubes (not illustrated) to run freely to and from the inlet 178 and outlet 180, respectively. Spring clips 186 and 188 as illustrated hold airtrap 110c in its proper position for operation. Spring clips 186 and 188 also allow for the ready insertion and removal of airtrap 110c.

With any of airtraps 110a to 110c, it is contemplated that that the inside surface of the wall forming the fluid chamber and the outside surface of the wall forming the fluid chamber have the same shape or roughly the same shape, e.g., with a constant wall thickness. This is illustrated in FIG. 4 for example where outer wall 118 of airtrap 110a, for example, has a constant thickness and the outside of housing 112 has a conical shape just as does the inside of conical housing 112. It should be appreciated however that "conical housing" additionally means just the inside surface of the chamber defining wall, where the outside surface could be any desired shape, e.g., cylindrical, rectangular, etc. In this latter embodiment, the spiraling flowpath is still obtained. The same is true for conical housing 152 of airtrap 110b. Additionally, any conical housing of the present disclosure may be partially conical, and not totally conical, e.g., having a flattened top or bottom.

The head section 174 and tubular tail section 176 of seahorse-shaped housing 172 can likewise look like a seahorse from the outside or only have the seahorse shape on the inside fluid-contacting surface. If the seahorse shape is provided only on the inside, fluid-contacting surface, the outer surface of housing 172 may instead be cylindrical or rectangular, for example. The flowpath of fluid through head section 174 and tubular tail section 176 is the same regardless.

The following chart sets forth certain example performance and physical characteristics comparing and contrasting the different airtraps 110a to 110c. Regarding the ability to remove air, airtraps 110a and 110c both performed very well, while airtrap 110c removed somewhat less air, but still performed well.

Regarding the amount of air that each airtrap can hold, airtraps 110a to 110c again perform better than airtrap 110b in the example illustrated below. Air trapping saturation volume is the volume of air that each airtrap 110a to 110c can store in its upper chamber (without air removal) before the air starts to become reinfused into the blood or other physiological fluid. Thus, if an entire treatment is only expected to produce 7.0 ml of air, then airtraps 110a and 110c may be used without any of the air removal techniques discussed herein. Airtrap 110b would however need some type of manual, passive or active air removal during treatment. If the entire treatment is expected instead to produce 15.0 ml of air, then each airtrap 110a to 110c would require some type of manual, passive or active air removal during treatment.

A smaller amount of blood volume is better generally because there is less blood to rinse back to the patient after treatment and if for some reason blood cannot be rinsed back to the patient, perhaps after a more severe alarm event, there is less blood trapped in the blood set. For other physiological fluids, e.g., dialysis fluid, water, saline, or liquid drug, airtrap volume is not as important. Regarding fluid volume in the examples below, airtrap 110b has the lowest volume, while airtrap 110a has around twice the volume as airtrap 110b.

Other factors besides those shown in the below chart include manufacturability and the ability to house or have air removal structure. Regarding these features, airtrap 110a is likely the most desirable. Airtrap 110a has a relatively simple shape compared with airtraps 110b and 110c, likely making airtrap 110a easier to mold and manufacture. Regarding air removal, passive air removal is likely the most desirable. Manual air removal as its same implies needs manual attention. Active air removal requires more equipment, such as an air pump and valve, e.g., solenoid or pneumatically operated valve. Passive air removal operates automatically like active air removal but needs no automatic actuation. The example structures discussed above for providing passive air removal are likely easiest to implement onto airtrap 110a. Airtrap 110a may employ flat top 114, which provides a convenient location for valve assembly 130 and hydrophobic filter 140.

Performance/Physical Characteristics Chart

|  | Trap 110a (FIGS. 3, 4) | Trap 110b (FIGS. 5, 6) | Trap 110c (FIGS. 7, 8, 9) |
|---|---|---|---|
| Air Trapped (%) | 97 | 86 | 100 |
| Air Trapping Saturation Volume (ml) | 9.0 | 5.8 | 11.9 |
| Blood (Liquid) Volume (ml) | 32.9 | 15.3 | 20.2 |

Additional Alternative Embodiments

As discussed above, any of airtraps 110a to 110c may be used in a blood treatment system 10, e.g., as part of a blood set 100 and/or within dialysis fluid circuit 70. In an alternative embodiment illustrated in connection with FIG. 10, any of airtraps 110a to 110c may be operated instead with an automated peritoneal dialysis ("APD") machine 190. APD machine 190 is sometimes called a cycler because it typically performs multiple drain, fill and dwell cycles. During drain cycles, APD machine 190 places a patient line 192 under negative pressure to pull used dialysate from a patient's peritoneal cavity. The patient line 192 is in fluid communication with a disposable cassette 194, which operates with APD machine 190 to pump peritoneal dialysis fluid to and from patient 12.

Patient line 192, disposable cassette 194 may form an overall disposable set along with a drain bag 196, one or more supply bags 198 and associated tubing. During fill cycles, APD machine 190 operating disposable cassette 194 places patient line 192 under positive pressure to push new dialysate from the machine to the patient's peritoneal cavity. During the dwell cycles, peritoneal dialysis fluid is left to dwell within the patient's peritoneal cavity.

Any of airtraps 110a to 110c may be placed in patient line 192, for example, at or near APD machine 190, so that airtraps 110a to 110c may be mounted in their proper operating positions and orientations on the chassis of APD machine 190. Airtraps 110a to 110c may each be mounted to the chassis of machine 190 via any of the structures and methodology discussed above for blood treatment machine 90. The cassette and patient line 192 for APD machine 190 is typically single use, so airtraps 110a to 110c for this application may simply trap and hold air over the course of treatment. It is contemplated however that airtraps 110a to 110c for APD machine 190 may alternatively employ manual air removal (e.g., via a septum) or passive air removal (e.g., via a filter and check valve).

When APD machine 190 is pulling used dialysis fluid from patient 12 via patient line 192, the fluid within the patient line is under negative pressure. In this instance, air may not be removed as easily within airtraps 110a to 110c. Importantly, however, when APD machine 190 is pushing fresh dialysis fluid to patient 12 via patient line 192, the fluid within the patient line is under positive pressure. In this more critical instance (because fluid is being delivered to patient 12), air is removed readily within airtraps 110a to 110c.

Figure 10:
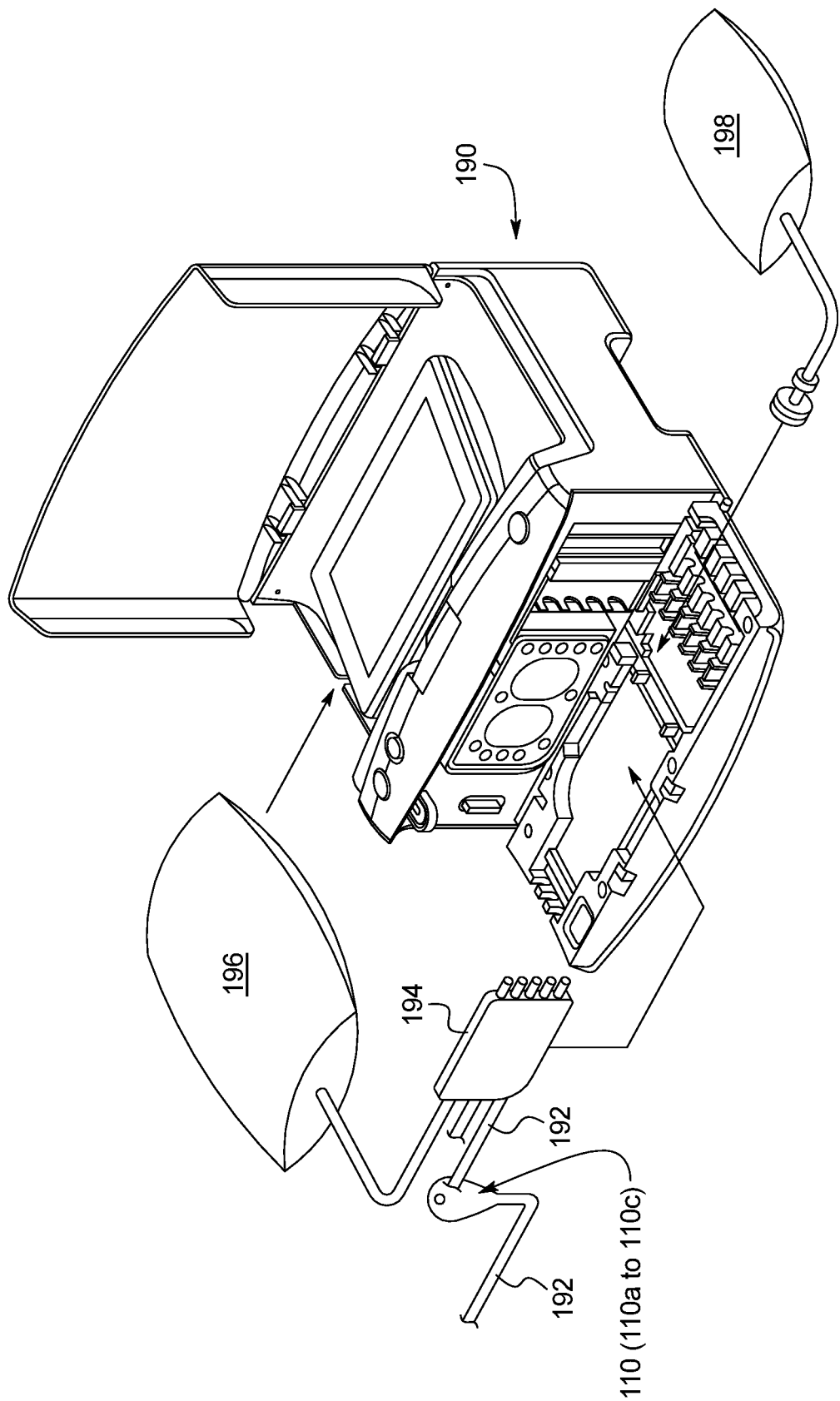
FIG. 10 is a perspective view illustrating any of the airtraps described herein operating with a peritoneal dialysis fluid set for use with an automated peritoneal dialysis machine.

While FIG. 10 illustrates airtraps 110a to 110c operating with an APD machine 190, it should be appreciated however that airtraps 110a to 110 could alternatively be used with a continuous ambulatory peritoneal dialysis set ("CAPD", not illustrated), which is manual peritoneal dialysis. Here, the patient is instructed to temporarily mount or attach airtraps 110a to 110c to a structure, such as a tabletop, so as to be maintained in a proper operating orientation during treatment. Airtraps 110a to 110c may be provided with structures, e.g., spring-loaded clamps for doing so.

Figure 11:
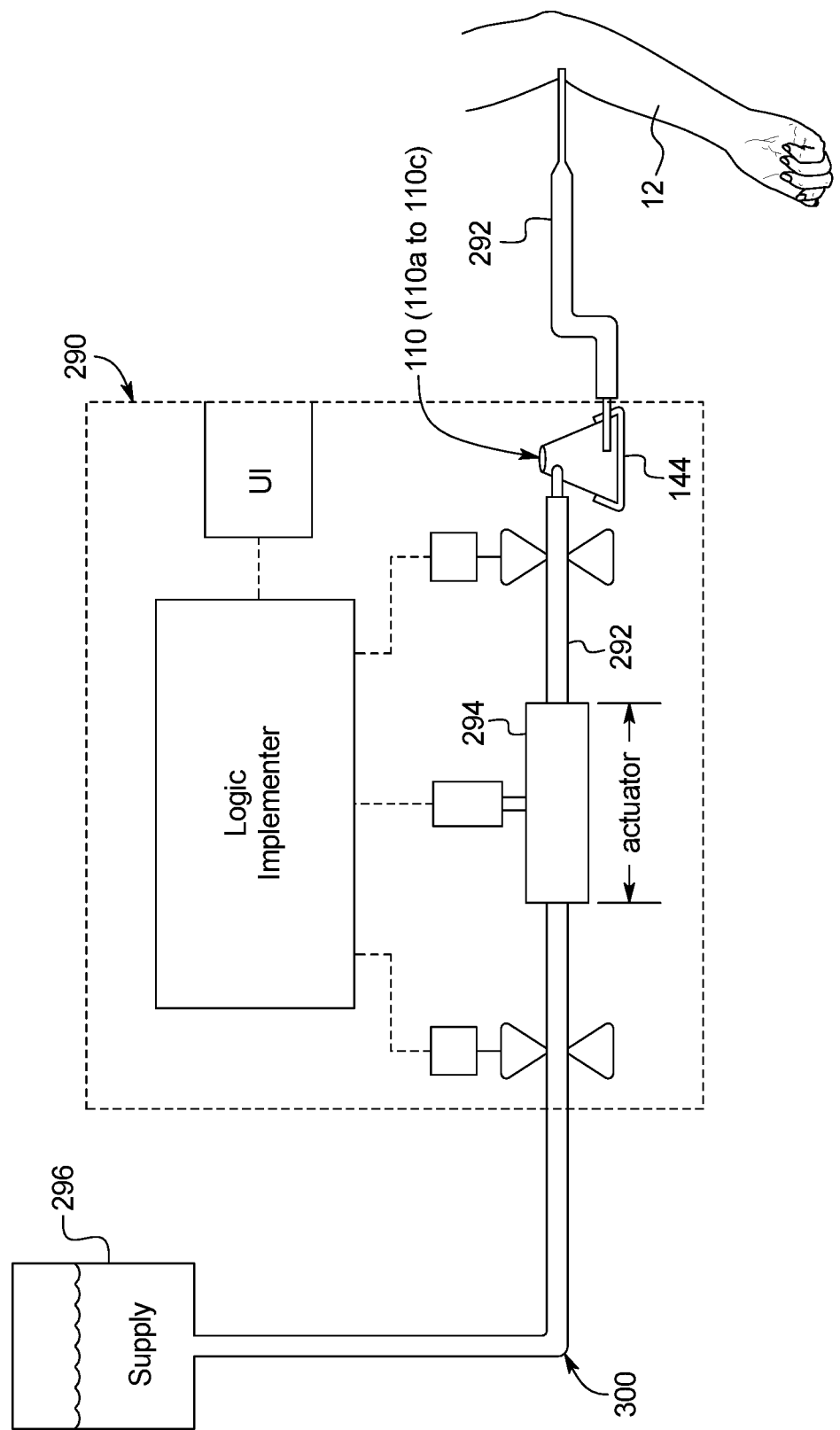
FIG. 11 is an elevation view illustrating any of the airtraps described herein operating with a drug delivery set for use with an infusion pump or drug delivery machine.

In a further alternative embodiment illustrated in connection with FIG. 11, any of airtraps 110a to 110c may be operated instead with an infusion pump 290 for administering one or more drugs to a patient via a drug delivery line 292. Infusion pump 290 may for example be a large volume infusion pump ("LVP"), which typically employs a rotary or peristaltic pump actuator or a shuttle pump actuator 294. Infusion pump 290 may alternatively be a syringe pump, which employs a syringe pump actuator 294. Drug delivery line 292 in the illustrated embodiment forms a drug delivery set 300 along with a source 296 of intravenous drug (which may be a bagged source, syringe source or other suitable source).

Any of airtraps 110a to 110c may be placed in patient line drug delivery line 292 downstream of pump actuator 294, for example, at or near infusion pump 290, so that airtraps 110a to 110c may be mounted in their proper operating positions and orientations on the chassis of infusion pump 290. Airtraps 110a to 110c may each be mounted to the chassis of infusion pump 290 via any of the structures and methodology discussed above for blood treatment machine 90. The pumping set including drug delivery line 292 for infusion pump 290 is typically single use, so airtraps 110a to 110c for this application may simply trap and hold air over the course of treatment. It is contemplated however that airtraps 110a to 110c for infusion pump 290 may alternatively employ manual air removal (e.g., via a septum) or passive air removal (e.g., via a filter and check valve).

Drug delivery line 292 downstream of pump actuator 294 is typically only under positive pressure to push one or more drug to patient 12. Here, air is removed readily from the one or more drug within airtraps 110a to 110c.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An airtrap for a fluid comprising:
    a conical housing having a radius that increases from a top to a bottom of the conical housing when the housing is positioned for operation;
    a medical or physiological fluid inlet located at an upper portion of the conical housing, wherein a solid and continuous bottom wall of the conical housing rises within an outer conical wall of the conical housing to form a solid and continuous inner conical wall inside of the outer conical wall;
    a medical or physiological fluid outlet located within a lower portion of the outer conical wall of the conical housing, the inlet and the outlet positioned and arranged so that fluid spirals in an increasing arc around an inside of the conical housing downwardly from the inlet to the outlet; and
    a gas collection area located at the upper portion of the conical housing.

2. The airtrap of claim 1, which includes a gas release valve located at an opening in the upper portion of the conical housing.

3. The airtrap of claim 2, wherein the gas release valve is a check valve.

4. The airtrap of claim 2, wherein the gas release valve includes a seal that stretches to open under gas pressure and self-closes once the gas pressure is released.

5. The airtrap of claim 1, which includes a hydrophobic filter located beneath an opening in the upper portion of the conical housing.

6. The airtrap of claim 1, wherein the inlet is horizontally disposed when the airtrap is positioned for operation.

7. The airtrap of claim 1, wherein the outlet is at least substantially horizontally disposed when the airtrap is positioned for operation, and wherein the outlet is formed by the outer conical wall.

8. The airtrap of claim 1, wherein the top of the conical housing at the upper portion is flat and defines a gas release outlet.

9. The airtrap of claim 1, wherein an angle of the inner conical wall relative to horizontal is less than an angle of the outer conical wall relative to horizontal.

10. The airtrap of claim 1, which is arranged such that the fluid spirals around an outside of the inner conical wall downwardly from the inlet to the outlet.

11. The airtrap of claim 1, wherein the bottom wall helps the fluid to spiral around the inside of the conical housing.

12. The airtrap of claim 1, wherein the gas collection area is located at an upper, central portion of the conical housing.

13. The airtrap of claim 1, which includes structure for being mounted in position for operation.

14. A renal therapy blood treatment system comprising:
a blood pump; and
a blood set for operation with the blood pump, the blood set having an airtrap including
a conical housing including an outer conical wall having a radius that increases from a top to a bottom of the conical housing when the housing is positioned for operation, wherein a solid and continuous bottom wall of the conical housing rises within the outer conical wall of the conical housing to form a solid and continuous inner conical wall inside of the outer conical wall,
a blood inlet located at an upper portion of the conical housing,
a blood outlet located within a lower portion of the outer conical wall of the conical housing, the inlet and the outlet positioned and arranged so that blood spirals around an inside of the conical housing downwardly from the inlet to the outlet, and
a gas collection area located at an upper portion of the conical housing.

15. The renal therapy blood treatment system of claim 14, wherein the blood set includes an arterial line and a venous line, and wherein the airtrap is located in the venous line.

16. The renal therapy blood treatment system of claim 14, which includes a dialysis fluid circuit, and wherein the airtrap is located in the dialysis fluid circuit.

17. The renal therapy blood treatment system of claim 14, which includes a chassis housing the blood pump and including a bracket for removeably mounting the airtrap in position for operation.

18. The renal therapy blood treatment system of claim 14, wherein the blood set is configured to be connected to a patient, and wherein the airtrap aims to prevent air from reaching the patient.

19. A peritoneal dialysis system comprising:
a peritoneal dialysis fluid pump; and
a disposable cassette for operation with the peritoneal dialysis fluid pump, the disposable cassette in fluid communication with a patient line having an airtrap including
a conical housing including an outer conical wall having a radius that increases from a top to a bottom of the conical housing when the housing is positioned for operation, wherein a solid and continuous bottom wall of the conical housing rises within the outer conical wall of the conical housing to form a solid and continuous inner conical wall inside of the outer conical wall,
a peritoneal dialysis fluid inlet located at an upper portion of the conical housing,
a peritoneal dialysis fluid outlet located within a lower portion of the outer conical wall of the conical housing, the inlet and the outlet positioned and arranged so that peritoneal dialysis fluid spirals around an inside of the conical housing downwardly from the inlet to the outlet, and
a gas collection area located at an upper portion of the conical housing.

20. The peritoneal dialysis system of claim 19, which includes a chassis housing the peritoneal dialysis fluid pump and including a bracket for removeably mounting the airtrap in position for operation.

21. The peritoneal dialysis system of claim 19, wherein the patient line is configured to be connected to a patient, and wherein the airtrap aims to prevent air from reaching the patient.

22. An infusion pump system comprising:
a drug delivery pump; and
a drug delivery set for operation with the drug delivery pump, the drug delivery set including a drug delivery line having an airtrap, the airtrap including
a conical housing including an outer conical wall having a radius that increases from a top to a bottom of the conical housing when the housing is positioned for operation, wherein a solid and continuous bottom wall of the conical housing rises within the outer conical wall of the conical housing to form a solid and continuous inner conical wall inside of the outer conical wall,
an intravenous drug inlet located at an upper portion of the conical housing,
an intravenous drug outlet located within a lower portion of the outer conical wall of the conical housing, the inlet and the outlet positioned and arranged so that an intravenous drug spirals around an inside of the conical housing downwardly from the inlet to the outlet, and
a gas collection area located at an upper portion of the conical housing.

23. The infusion pump system of claim 22, which includes a chassis housing the drug delivery pump and including a bracket for removeably mounting the airtrap in position for operation.

24. The infusion pump system of claim 22, wherein the drug delivery line is configured to be connected to a patient, and wherein the airtrap aims to prevent air from reaching the patient.

* * * * *